(12) United States Patent
Omori et al.

(10) Patent No.: US 10,532,341 B2
(45) Date of Patent: Jan. 14, 2020

(54) PARTICULATE WATER ABSORBING AGENT

(71) Applicant: NIPPON SHOKUBAI CO., LTD., Osaka-shi, Osaka (JP)

(72) Inventors: Kohei Omori, Hyogo (JP); Kazushi Torii, Hyogo (JP); Nobuya Tanaka, Hyogo (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 54 days.

(21) Appl. No.: 15/739,798

(22) PCT Filed: Jul. 1, 2016

(86) PCT No.: PCT/JP2016/069715
§ 371 (c)(1),
(2) Date: Dec. 26, 2017

(87) PCT Pub. No.: WO2017/002972
PCT Pub. Date: Jan. 5, 2017

(65) Prior Publication Data
US 2018/0161756 A1    Jun. 14, 2018

(30) Foreign Application Priority Data
Jul. 1, 2015    (JP) .................................. 2015-132985

(51) Int. Cl.
  *B01J 20/26*    (2006.01)
  *B01J 20/28*    (2006.01)
  (Continued)

(52) U.S. Cl.
  CPC ........... *B01J 20/261* (2013.01); *B01J 20/267* (2013.01); *B01J 20/28004* (2013.01);
  (Continued)

(58) Field of Classification Search
  CPC ........ B01J 20/26; B01J 20/261; B01J 20/267; B01J 20/28; B01J 20/28004;
  (Continued)

(56) References Cited

U.S. PATENT DOCUMENTS

| 655,239 A | 8/1900 | Jespersen |
| 4,734,478 A * | 3/1988 | Tsubakimoto .......... A61L 15/18 527/300 |

(Continued)

FOREIGN PATENT DOCUMENTS

| EP | 0 629 411 A1 | 12/1994 |
| EP | 0940149 A1 | 9/1999 |

(Continued)

OTHER PUBLICATIONS

Japanese Office Action and English translation thereof dated Feb. 12, 2019.

(Continued)

*Primary Examiner* — Cam N. Nguyen
(74) *Attorney, Agent, or Firm* — Harness, Dickey and Pierce, P.L.C.

(57) ABSTRACT

A particulate water absorbing agent having a polyacrylic acid (salt)-based water-absorbing resin as a main component, being surface-crosslinked and satisfying physical properties (1) to (3) below: (1) a proportion of particles with a particle diameter of not less than 150 μm and less than 850 μm is not less than 90% by weight; (2) an elastic modulus index (EMI) of particles with a particle diameter of not less than 500 μm and less than 600 μm is not less than 5500; and (3) a recovery rate defined as Rec.CRC/CRC is 1.05 to 1.20, the particulate water absorbing agent being particularly useful for absorbent articles.

15 Claims, 6 Drawing Sheets

(51) Int. Cl.
*C08J 3/12* (2006.01)
*C08J 3/24* (2006.01)

(52) U.S. Cl.
CPC ... *B01J 20/28011* (2013.01); *B01J 20/28016* (2013.01); *C08J 3/245* (2013.01); *C08J 2333/02* (2013.01)

(58) Field of Classification Search
CPC .. B01J 20/28011; B01J 20/28016; C08J 3/12; C08J 3/24; C08J 3/245
See application file for complete search history.

(56) References Cited

U.S. PATENT DOCUMENTS

| | | | |
|---|---|---|---|
| 4,755,562 A | 7/1988 | Alexander et al. | |
| 4,783,510 A | 11/1988 | Saotome | |
| 4,824,901 A | 4/1989 | Alexander et al. | |
| 5,250,640 A | 10/1993 | Irie et al. | |
| 5,380,808 A | 1/1995 | Sumiya et al. | |
| 5,409,771 A | 4/1995 | Dahmen et al. | |
| 5,610,208 A | 3/1997 | Dairoku et al. | |
| 5,672,633 A | 9/1997 | Brehm et al. | |
| 6,239,230 B1 | 5/2001 | Eckert et al. | |
| 6,265,488 B1 | 7/2001 | Fujino et al. | |
| 6,297,133 B1 | 10/2001 | Funk et al. | |
| 6,297,319 B1 | 10/2001 | Nagasuna et al. | |
| 6,372,852 B2 | 4/2002 | Hitomi et al. | |
| 6,472,478 B1 | 10/2002 | Funk et al. | |
| 6,605,673 B1 | 8/2003 | Mertens et al. | |
| 6,620,889 B1 | 9/2003 | Mertens et al. | |
| 6,657,015 B1 | 12/2003 | Riegel et al. | |
| 6,809,158 B2* | 10/2004 | Ikeuchi | C08J 3/245 525/329.1 |
| 7,201,941 B2 | 4/2007 | Irie et al. | |
| 7,638,570 B2* | 12/2009 | Torii | A61L 15/60 524/430 |
| 8,138,292 B2* | 3/2012 | Matsumoto | B65B 1/08 526/223 |
| 8,198,209 B2* | 6/2012 | Torii | A61L 15/18 428/326 |
| 8,252,715 B2* | 8/2012 | Torii | A61F 13/53 502/402 |
| 8,424,786 B2* | 4/2013 | Ishizaki | B65B 1/08 241/23 |
| 8,822,373 B2* | 9/2014 | Fujimaru | A61L 15/24 502/400 |
| 8,846,823 B2* | 9/2014 | Nakamura | A61L 15/60 502/402 |
| 9,006,134 B2* | 4/2015 | Nagasawa | A61F 13/53 502/400 |
| 2003/0207997 A1 | 11/2003 | Mertens et al. | |
| 2004/0071966 A1 | 4/2004 | Inger et al. | |
| 2004/0176544 A1 | 9/2004 | Mertens et al. | |
| 2004/0176557 A1 | 9/2004 | Mertens et al. | |
| 2005/0020780 A1 | 1/2005 | Inger et al. | |
| 2007/0129495 A1 | 6/2007 | Mertens et al. | |
| 2007/0141338 A1* | 6/2007 | Ishizaki | C08J 3/12 428/402 |
| 2007/0161759 A1 | 7/2007 | Riegel et al. | |
| 2008/0021131 A1 | 1/2008 | Mertens et al. | |
| 2008/0281049 A1 | 11/2008 | Wendker et al. | |
| 2009/0036855 A1* | 2/2009 | Wada | A61F 13/531 604/372 |
| 2009/0182294 A1* | 7/2009 | Ikeuchi | A61L 15/60 604/368 |
| 2009/0208748 A1 | 8/2009 | Torii et al. | |
| 2009/0275470 A1 | 11/2009 | Nagasawa et al. | |
| 2009/0298685 A1 | 12/2009 | Torii et al. | |
| 2009/0318885 A1* | 12/2009 | Dairoku | A61L 15/24 604/367 |
| 2010/0041550 A1 | 2/2010 | Riegel et al. | |
| 2011/0040044 A1 | 2/2011 | Motoyama et al. | |
| 2011/0042612 A1 | 2/2011 | Riegel et al. | |
| 2011/0112252 A1 | 5/2011 | Blei et al. | |
| 2011/0257341 A1 | 10/2011 | Riegel et al. | |
| 2012/0267570 A1* | 10/2012 | Shi | A61L 15/60 252/194 |
| 2012/0305842 A1 | 12/2012 | Torii et al. | |
| 2013/0026412 A1 | 1/2013 | Machida et al. | |
| 2014/0058346 A1* | 2/2014 | Wada | A61L 15/42 604/368 |
| 2015/0210843 A1 | 7/2015 | Kimura et al. | |
| 2015/0217270 A1* | 8/2015 | Ueda | C08J 3/245 252/194 |
| 2017/0044332 A1 | 2/2017 | Kimura et al. | |
| 2017/0203279 A1 | 7/2017 | Murakami et al. | |
| 2017/0216817 A1 | 8/2017 | Torii et al. | |
| 2018/0094131 A1 | 4/2018 | Tanaka et al. | |

FOREIGN PATENT DOCUMENTS

| | | |
|---|---|---|
| EP | 1 191 051 A2 | 3/2002 |
| EP | 1824910 A2 | 8/2007 |
| JP | 4-175319 | 6/1992 |
| JP | 4-46617 | 7/1992 |
| JP | 5-112654 | 5/1993 |
| JP | 7-088171 | 4/1995 |
| JP | 2009-531467 | 9/2009 |
| JP | 2011527360 A | 10/2011 |
| KR | 2011/0049072 A | 5/2011 |
| WO | WO-92/000108 A1 | 1/1992 |
| WO | WO-1998/049221 A1 | 11/1998 |
| WO | WO-00/46260 A1 | 8/2000 |
| WO | WO-00/53644 A1 | 9/2000 |
| WO | WO-00/53664 A1 | 9/2000 |
| WO | WO-01/074913 A1 | 10/2001 |
| WO | WO-02/20068 A1 | 3/2002 |
| WO | WO-02/22717 A1 | 3/2002 |
| WO | WO-02/100451 A2 | 12/2002 |
| WO | WO-2005/080479 A1 | 9/2005 |
| WO | WO-2006033477 A1 | 3/2006 |
| WO | WO-2006/062258 A2 | 6/2006 |
| WO | WO-2007/065834 A1 | 6/2007 |
| WO | WO-2008/092842 A1 | 8/2008 |
| WO | WO-2008/092843 A1 | 8/2008 |
| WO | WO-2008/110524 A1 | 9/2008 |
| WO | WO-2009/080611 A2 | 7/2009 |
| WO | WO-09/125849 A1 | 10/2009 |
| WO | WO-2011/040530 A1 | 4/2011 |
| WO | WO-2011/117263 A1 | 9/2011 |
| WO | WO-2014041969 A1 | 3/2014 |
| WO | WO-2016/006132 A1 | 1/2016 |
| WO | WO-2016052537 A1 | 4/2016 |
| WO | WO-2016/158976 A1 | 10/2016 |

OTHER PUBLICATIONS

International Search Report dated Sep. 20, 2016.
International Preliminary Report on Patentability dated Jan. 2, 2018.
Extended European Search Report dated Oct. 17, 2018.

* cited by examiner

PARTICULATE WATER ABSORBING AGENT

TECHNICAL FIELD

The present invention relates to a particulate water absorbing agent. More specifically, the present invention relates to a particulate water absorbing agent that exhibits a particularly excellent water absorbing property and liquid permeability.

BACKGROUND ART

Water-absorbing resin (super absorbent polymer [SAP]) is a water-swellable, water-insoluble polymer gelling agent. Water-absorbing resin is used in various applications including use in absorbent articles such as disposable diapers and sanitary napkins, agricultural and horticultural water retaining agents, and industrial waterproofing agents.

In recent years, these sanitary products such as disposable diapers, sanitary napkins, and incontinence pads have become higher in functionality and thinner, so that a larger amount of water-absorbing agent tends to be used in a single sanitary product, and a water-absorbing agent tends to be contained in a larger amount with respect to the entire absorbent body that is made of, for example, a water-absorbing agent and hydrophilic fiber. Specifically, studies have been carried out on, with use of a smaller amount of hydrophilic fiber with a small bulk specific gravity and a larger amount of a water-absorbing agent with an excellent water absorbency and a large bulk specific gravity, reducing the thickness of a sanitary product without reducing the amount of water absorption by increasing the proportion of a water-absorbing agent in an absorbent body.

Though such a sanitary product, in which the content of a water-absorbing agent is increased by decreasing the proportion of hydrophilic fiber, tends to be preferable from the viewpoint of simply storing a liquid, a problem arises to the contrary in consideration of distribution and diffusion of a liquid in actual use of the sanitary product.

A water-absorbing agent that absorbs water turns into a soft gel-like water-absorbing agent. Thus, in a case where such a water-absorbing agent that is large in amount per unit volume has absorbed water, a gel blocking phenomenon occurs. This phenomenon causes a considerable reduction in diffusibility of a liquid in a sanitary product. As a result, that part of the water-absorbing agent which is distant from a central area of the sanitary product and which is therefore difficult for the liquid to reach does not effectively function. This prevents the effect of increasing the water-absorbing agent content from being sufficiently exhibited, so that the sanitary product in actual use has an absorbing capability that is much lower than the theoretical level.

In order that such a problem is avoided and the absorbing capability of an absorbent body is maintained, the ratio between hydrophilic fiber and a water-absorbing agent is inevitably restricted, so that the thinning of a sanitary product is also limited.

Examples of indexes used to evaluate an reduction of gel blocking in a sanitary product include a fluid retention capacity under load (absorbency against pressure [AAP] or performance under pressure [PUP]), indicative of a water absorbing property under load, and a saline flow conductivity (hereinafter abbreviated as "SFC"; see Patent Literature 1).

As publicly known techniques for reducing gel blocking, there have been known the following techniques: a technique of changing the crosslinking densities inside and outside of a water-absorbing agent by a surface treatment; a technique that combines a surface treatment with inorganic compound(s) as a liquid permeability improving agent such as inorganic microparticles and a polyvalent metal salt and/or cationic polymer compound(s) as a liquid permeability improving agent; a technique for improving water absorption performance, particularly liquid diffusibility; and a technique for controlling a reaction environment of a surface-crosslinking treatment (see Patent Literatures 1 to 39).

Recent years have also seen a tendency of an increase in the use of disposable diapers in developing countries. In such less rich countries, there may be an increasing demand in the future to wash a disposable diaper, used once, with water lightly and use it again from the viewpoint of reducing the cost of purchasing diapers. Further, developed countries now have aging society. Elderly people in recent years have a larger proportion of drinkers than in the past. Among drinkers, those who wear a diaper habitually may first discharge urine that is thin like water and then discharge normal urine.

CITATION LIST

Patent Literature

[Patent Literature 1]
U.S. Pat. No. 6,297,319 (Publication Date: Aug. 2, 2001)
[Patent Literature 2]
U.S. Pat. No. 6,372,852 (Publication Date: Apr. 16, 2002)
[Patent Literature 3]
U.S. Pat. No. 6,265,488 (Publication Date: Jul. 24, 2001)
[Patent Literature 4]
U.S. Pat. No. 6,809,158 (Publication Date: Aug. 26, 2004)
[Patent Literature 5]
U.S. Pat. No. 4,734,478 (Publication Date: Mar. 29, 1988)
[Patent Literature 6]
U.S. Pat. No. 4,755,562 (Publication Date: Jul. 5, 1988)
[Patent Literature 7]
U.S. Pat. No. 4,824,901 (Publication Date: Apr. 25, 1989)
[Patent Literature 8]
U.S. Pat. No. 6,239,230 (Publication Date: Mar. 29, 2001)
[Patent Literature 9]
U.S. Pat. No. 6,559,239 (Publication Date: Mar. 6, 2003)
[Patent Literature 10]
U.S. Pat. No. 6,472,478 (Publication Date: Oct. 29, 2002)
[Patent Literature 11]
U.S. Pat. No. 6,657,015 (Publication Date: Dec. 2, 2003)
[Patent Literature 12]
U.S. Pat. No. 5,672,633 (Publication Date: Sep. 30, 1997)
[Patent Literature 13]
European Patent Application Publication No. 0940149 (Publication Date: Sep. 8, 1999)
[Patent Literature 14]
International Publication No. 2006/033477 pamphlet (Publication Date: Mar. 30, 2006)
[Patent Literature 15]
U.S. Pat. No. 7,201,941 (Publication Date: Mar. 3, 2005)
[Patent Literature 16]
U.S. Pat. No. 4,783,510 (Publication Date: Nov. 3, 1988)
[Patent Literature 17]
European Patent No. 1824910 (Publication Date: Aug. 29, 2007)
[Patent Literature 18]
International Publication No. 2002-100451 pamphlet (Publication Date: Dec. 19, 2002)

[Patent Literature 19]
U.S. Pat. No. 5,610,208 (Publication Date: Mar. 11, 1997)
[Patent Literature 20]
International Publication No. 92/000108 pamphlet (Publication Date: Sep. 1, 1992)
[Patent Literature 21]
International Publication No. 98/49221 pamphlet (Publication Date: Nov. 5, 1998)
[Patent Literature 22]
International Publication No. 00/53644 pamphlet (Publication Date: Sep. 14, 2000)
[Patent Literature 23]
International Publication No. 00/53664 pamphlet (Publication Date: Sep. 14, 2000)
[Patent Literature 24]
International Publication No. 01/074913 pamphlet (Publication Date: Oct. 11, 2001)
[Patent Literature 25]
International Publication No. 2002/020068 pamphlet (Publication Date: Mar. 14, 2002)
[Patent Literature 26]
International Publication No. 2002/022717 pamphlet (Publication Date: Mar. 21, 2002)
[Patent Literature 27]
International Publication No. 2005/080479 pamphlet (Publication Date: Sep. 1, 2005)
[Patent Literature 28]
International Publication No. 2007/065834 pamphlet (Publication Date: Jun. 14, 2007)
[Patent Literature 29]
International Publication No. 2008/092842 pamphlet (Publication Date: Aug. 7, 2008)
[Patent Literature 30]
International Publication No. 2008/092843 pamphlet (Publication Date: Aug. 7, 2008)
[Patent Literature 31]
International Publication No. 2008/110524 pamphlet (Publication Date: Sep. 18, 2008)
[Patent Literature 32]
International Publication No. 2009/080611 pamphlet (Publication Date: Jul. 2, 2009)
[Patent Literature 33]
Japanese Examined Patent Application Publication, Tokukouhei, No. 4-46617 (Publication Date: Nov. 14, 1986)
[Patent Literature 34]
International Publication No. 00/46260 pamphlet (Publication Date: Aug. 10, 2000)
[Patent Literature 35]
European Patent No. 1191051 specification (Publication Date: Mar. 27, 2002)
[Patent Literature 36]
International Publication No. 2011/117263 pamphlet (Publication Date: Sep. 29, 2011)
[Patent Literature 37]
International Publication No. 09/125849 pamphlet (Publication Date: Oct. 15, 2009)
[Patent Literature 38]
South Korean Patent No. 2011/0049072 specification (May 12, 2011)
[Patent Literature 39]
Japanese Translation of PCT International Application, Tokuhyo, No. 2011-527360 (Publication Date: Oct. 27, 2011)

SUMMARY OF INVENTION

Technical Problem

The background discussed above provides a prediction that there will be a rapidly increasing demand in the near future for a particulate water absorbing agent that in a case where the particulate water absorbing agent is used as an absorbent body for an absorbent article such as disposable diapers, maintains its liquid absorption speed and has only a small re-wet amount even after becoming swollen once.

Recent years have seen a growing number of elderly people who use diapers. There will be a need for a capability to absorb urine under a load that is heavier than the load assumed for a disposable diaper for babies. This provides another prediction that there will be a rapidly increasing demand in the near future for a particulate water absorbing agent that in a case where the particulate water absorbing agent is used as an absorbent body for an absorbent article such as disposable diapers, has an excellent absorption speed and only a small re-wet amount even under a high pressure.

Although the production methods disclosed in the above patent literatures achieve improvements in the liquid permeability and absorption capacity under load of water-absorbing resin, there have not been sufficient studies on improvements in the physical properties of water-absorbing resin that has been swollen once with deionized water. There is a need for further improvements in those physical properties. Further, there have not been sufficient studies on improvements in the absorbing performance under a heavy load. There is a need for further improvements in the physical property.

In view of the above, it is an object of an embodiment of the present invention to provide a particulate water absorbing agent that does not inhibit the absorbing performance of an absorbent article such as disposable diapers and that maintains the liquid permeability and fluid retention capacity under pressure even after a water-absorbing resin is used a plurality of times and the particulate water absorbing agent is used under a heavy load.

Solution to Problem

In order to attain the above object, the inventors of the present invention have conducted diligent research and thereby discovered that a particulate water absorbing agent which has a particular particle size distribution and whose ratio between the fluid retention capacity for physiological saline and the fluid retention capacity that the particulate water absorbing agent has in a case where the particulate water absorbing agent has been swollen with deionized water and immersed in physiological saline again is controlled within a particular range maintains its absorption speed and has only a small re-wet amount even under a heavy load even after becoming swollen and contracted once in a case where the particulate water absorbing agent is used as an absorbent body for an absorbent article such as disposable diapers. The inventors have consequently completed the present invention.

Specifically, a particulate water absorbing agent in accordance with an embodiment of the present invention is a particulate water absorbing agent having a polyacrylic acid (salt)-based water-absorbing resin as a main component, being surface-crosslinked and satisfying physical properties (1) to (3) below:

(1) a proportion of particles with a particle diameter of not less than 150 μm and less than 850 μm is not less than 90% by weight;

(2) an elastic modulus index (EMI) of particles with a particle diameter of not less than 500 μm and less than 600 μm is not less than 5500; and (3) a recovery rate defined as Rec.CRC/CRC is 1.05 to 1.20.

Further, an absorbent body in accordance with an embodiment of the present invention is an absorbent body, including the particulate water absorbing agent.

An absorbent article in accordance with an embodiment of the present invention is an absorbent article, including the particulate water absorbing agent.

Advantageous Effects of Invention

A particulate water absorbing agent in accordance with an embodiment of the present invention has a high fluid retention capacity under pressure and a high liquid permeability even after the particulate water absorbing agent has been swollen with deionized water. As described above, a particulate water absorbing agent in accordance with an embodiment of the present invention, an absorbent body including the particulate water absorbing agent, and an absorbent article including the particulate water absorbing agent each maintain its absorption speed and have only a small re-wet even under a heavy load even after the particulate water absorbing agent has been swollen once. This yields an effect of providing absorbent articles such as a disposable diaper, a sanitary napkin, and a blood absorbent for medical use each having more excellent physical properties.

DESCRIPTION OF EMBODIMENTS

Figure 1:
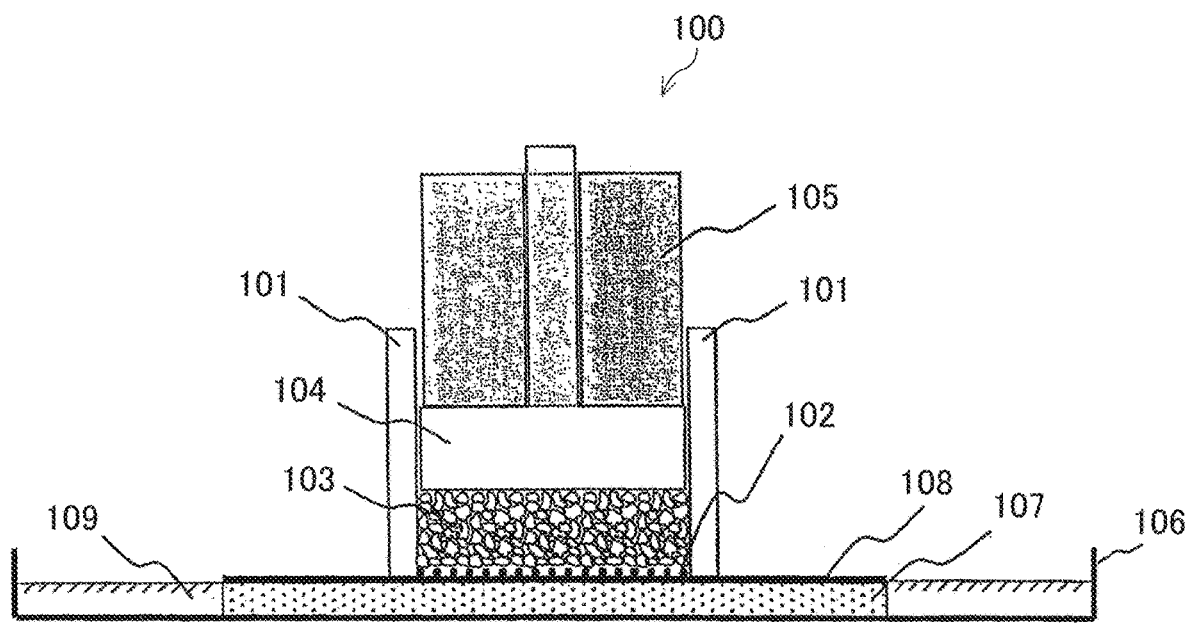
FIG. 1 is a cross-sectional view of a device for use in measuring a fluid retention capacity under pressure (AAP) and a recovery AAP (Rec.AAP).

The following description will discuss in detail a particulate water absorbing agent and a method for producing the particulate water absorbing agent in accordance with an embodiment of the present invention. The present invention is, however, not limited in scope to the description below, and may be altered from the examples below and practiced as appropriate as long as such alteration is not a departure from the scope of the present invention.

Specifically, the present invention should not be construed as being limited to the embodiments below, and may be modified in many ways within the scope of the claims below. The technical scope of the present invention may encompass any modifications obtainable by appropriately combining technical means disclosed in different embodiments.

[1] Definitions of Terms (1-1) "Water-Absorbing Resin"

The term "water-absorbing resin" as used for an embodiment of the present invention means a water-swellable, water-insoluble polymer gelling agent. The expression "water-swellable" indicates a centrifuge retention capacity (CRC) as defined in ERT 441.2-02 of not less than 5 g/g. The expression "water-insoluble" indicates a water-soluble component (Ext) as defined in ERT 470.2-02 of not more than 50% by weight.

The water-absorbing resin can be designed as appropriate according to its purpose of use, and is not limited to any particular one. The water-absorbing resin is preferably a hydrophilic crosslinked polymer that has been obtained by crosslinking and polymerizing unsaturated monomers each of which has a carboxyl group. Moreover, the water-absorbing resin is not limited to a form in which the water-absorbing resin is wholly (that is, 100 weight %) a polymer, and can be a water-absorbing resin that is surface-crosslinked or a water-absorbing resin composition that contains an additive and/or the like within a range in which the above-described performance is maintained.

The "water-absorbing resin" above is a resin that has been obtained by crushing the hydrophilic crosslinked polymer into powder form. For convenience, a water-absorbing resin that has not been surface-treated or surface-crosslinked is herein referred to as "water-absorbing resin powder", whereas a water-absorbing resin that has been surface-treated or surface-crosslinked is herein referred to as "water-absorbing resin particles".

Further, either a water-absorbing resin that varies in form obtained in each step (examples of the form of the water-absorbing resin include a sheet form, a fiber form, a film form, and a gel form) or a water-absorbing resin composition that contains an additive and/or the like is herein collectively referred to as "water-absorbing resin". A water-absorbing resin as a finished product is herein referred to as "particulate water absorbing agent".

(1-2) "Polyacrylic Acid (Salt)"

The term "polyacrylic acid (salt)" as used for an embodiment of the present invention means a polymer that has a graft component as necessary and contains, as a main component, repeating units constituted by an acrylic acid, a salt thereof, or a combination thereof (the acrylic acid, the salt thereof, and the combination are herein collectively referred to as "acrylic acid (salt)").

Specifically, the term "polyacrylic acid (salt)" as used for an embodiment of the present invention is a polymer in which an acrylic acid (salt) essentially accounts for 50 mol % to 100 mol % in the total monomer content (except an internal crosslinking agent) to be polymerized, preferably a polymer in which an acrylic acid (salt) accounts for 70 mol % to 100 mol % in the total monomer content, even more preferably a polymer in which an acrylic acid (salt) accounts for 90 mol % to 100 mol % in the total monomer content, and especially even more preferably a polymer in which an acrylic acid (salt) accounts for substantially 100 mol % in the total monomer content.

Further, the polyacrylic acid salt which is used as a polymer essentially contains a water-soluble salt, and the water-soluble salt (neutralized salt) contains, as a main component, preferably a monovalent salt, more preferably an alkali metal salt or ammonium salt, even more preferably an alkali metal salt, and especially even more preferably a sodium salt.

(1-3) "EDANA" and "ERT"

The term "EDANA" is an acronym for the European Disposables and Nonwovens Associations. The term "ERT" is an acronym for EDANA Recommended Test Methods, which are European standard (de facto international standard) methods for measuring physical properties of water-absorbing resin. Note that unless otherwise specified, the measurement is carried out for an embodiment of the present invention in conformity with a master copy of the ERT (known literature: 2002 revised version).

(1-3-1) "CRC" (ERT 441.2-02)

The term "CRC" is an acronym for "centrifuge retention capacity", and refers to a fluid retention capacity of water-absorbing resin without pressure (herein referred to also as "fluid retention capacity"). Specifically, the CRC refers to a fluid retention capacity (unit: g/g) measured after 0.20 g of water-absorbing resin contained in a nonwoven fabric bag is immersed in a large excess of a 0.9 weight % aqueous sodium chloride solution for 30 minutes so as to be allowed to freely swell, and then the water-absorbing resin is drained in a centrifuge (250 G) for 3 minutes.

(1-3-2) "AAP" (ERT 442.2-02)

The term "AAP" is an acronym for "absorption against pressure", and refers to a fluid retention capacity of water-absorbing resin under pressure. Specifically, "AAP" refers to a fluid retention capacity (unit: g/g) measured after 0.90 g of water-absorbing resin has been swollen in a large excess of a 0.9 weight % aqueous sodium chloride solution for 1 hour under a load of 2.06 kPa (0.3 psi). ERT 442.2-02 uses the term "Absorption Under Pressure", which refers to substantially the same thing as "AAP". The load may be changed to 4.83 kPa (0.7 psi) according to the purpose.

(1-3-3) "Ext" (ERT 470.2-02)

The term "Ext" is an abbreviation for "Extractables", and refers to a water-soluble component (water-soluble component amount) of water-absorbing resin. Specifically, the Ext refers to the amount (unit: weight %) of a substance dissolved in an aqueous solution, the amount being obtained by adding 1.0 g of water-absorbing resin to 200 ml of a 0.9 weight % aqueous sodium chloride solution and stirring the resulting mixture at 500 rpm for 16 hours. The water-soluble component is measured by pH titration.

(1-3-4) "PSD" (ERT 420.2-02)

The term "PSD" is an acronym for "particle size distribution", and refers to a particle size distribution of water-absorbing resin which is measured by sieve classification. The weight average particle diameter (D50) and the logarithmic standard deviation ($\sigma\zeta$) of a particle size distribution are measured according to a method similar to the method described in "(3) Mass-Average Particle Diameter (D50) and Logarithmic Standard Deviation ($\sigma\zeta$) of Particle Diameter Distribution" disclosed in U.S. Pat. No. 7,638,570.

(1-4) Other Physical Properties (1-4-1) "SFC"

The term "SFC" as used for an embodiment of the present invention is an acronym for "saline flow conductivity", and refers to a liquid permeability (unit: $\times 10^{-7} \cdot cm^3 \cdot s \cdot g^{-1}$) of water-absorbing resin per a 0.69 weight % aqueous sodium chloride solution under a load of 2.07 kPa. A larger SFC value indicates a water-absorbing resin having a higher liquid permeability. "SFC" is measured in conformity with an SFC testing method described in the specification of U.S. Pat. No. 5,849,405.

(1-4-2) "FSR"

The term "FSR" as used for an embodiment of the present invention is an acronym for "free swell rate", and refers to a speed (unit: $g/(g \cdot s)$) at which 1 g of water-absorbing resin absorbs 20 g of a 0.9 weight % aqueous sodium chloride solution.

(1-4-3) "Vortex"

The term "Vortex" as used for an embodiment of the present invention is a water absorption time determined in conformity with the "Testing Method for Water Absorption Rate of Super Absorbent Polymers" described in JIS K7224. "Vortex" refers to a time period (unit: seconds) necessary for 2 g of water-absorbing resin to absorb 50 g of a 0.9 weight % aqueous sodium chloride solution.

(1-4-4) "Rec.CRC"

The term "Rec.CRC (recovery CRC)" as used for an embodiment of the present invention refers to a fluid retention capacity (unit: g/g) of water-absorbing resin without pressure which has been swollen with a 0.9 weight % aqueous sodium chloride solution after the water-absorbing resin was swollen once with deionized water and was then drained in a centrifuge (or was subjected to ethanol substitution and was then air-dried). A specific method of measurement will be described in the Examples section.

The present specification uses the term "recovery rate" to refer to the rate of Rec.CRC to CRC (Rec.CRC/CRC).

(1-4-5) "Rec.AAP"

The term "Rec.AAP (recovery AAP)" as used for an embodiment of the present invention refers to a fluid retention capacity under pressure (unit: g/g) which water-absorbing resin having been swollen with deionized water exhibits on a 0.9 weight % aqueous sodium chloride solution. A specific method of measurement will be described in the Examples section.

(1-4-6) "Rec.SFC"

The term "Rec.SFC (recovery SFC)" as used for an embodiment of the present invention refers to a liquid permeability (unit: $\times 10^{-7} \cdot cm^3 \cdot s \cdot g^{-1}$) that water-absorbing resin having been swollen with deionized water exhibits under a load of 2.07 kPa on a 0.69 weight % aqueous sodium chloride solution. A specific method of measurement will be described in the Examples section.

(1-4-7) Elastic Modulus Index

The term "elastic modulus index" as used for an embodiment of the present invention is a value obtained by correcting an elastic modulus on the basis of a theoretical surface area and CRC of swollen gel particles, and is a value that serves as an index for evaluation of the performance of water-absorbing resin. The present specification may use the acronym "EMI" to refer to "elastic modulus index". The term "swollen gel particles" refers to particles of a swollen gel prepared by swelling water-absorbing resin with deionized water. A specific method of measurement will be described in the Examples section.

(1-4-8) Diffusion Absorbency Period

The term "diffusion absorbency period" as used for an embodiment of the present invention refers to a water absorption time under pressure (unit: seconds) which either water-absorbing resin or water-absorbing resin that has been swollen with a 0.9 weight % aqueous sodium chloride solution has on 75 g of a 0.9 weight % aqueous sodium chloride solution. The present specification uses the term "first-time diffusion absorbency period" to refer to a time period in which the above aqueous solution is entirely absorbed by water-absorbing resin that has not been swollen, the term "second-time diffusion absorbency period" to refer to a time period in which, after the above aqueous solution is introduced the second time 10 minutes after the start of introducing the aqueous solution the first time, the aqueous solution is entirely absorbed by the water-absorbing resin that has been swollen once, and the term "third-time diffusion absorbency period" to refer to a time period in which, similarly 10 minutes after the start of introducing the aqueous solution the second time, the aqueous solution is entirely absorbed by the water-absorbing resin that has been swollen twice. A specific method of measurement will be described in the Examples section.

(1-5) Other

In the present specification, any range "X to Y" means "not less than X and not more than Y". "t (ton)", which is a unit of weight, means "metric ton". Moreover, unless otherwise specified, "ppm" means "ppm by weight". "weight" is synonymous with "mass", "weight %" is synonymous with "mass %", and "parts by weight" is synonymous with "parts by mass". Further, " . . . acid (salt)" means " . . . acid and/or salt thereof", and "(meth)acrylic" means "acrylic and/or methacrylic".

[2] Physical Properties of Particulate Water Absorbing Agent

A particulate water absorbing agent in accordance with an embodiment of the present invention is a particulate water absorbing agent having a polyacrylic acid (salt)-based water-absorbing resin as a main component, being surface-crosslinked and satisfying physical properties (1) to (3) below:

(1) a proportion of the particles with a particle diameter of not less than 150 μm and less than 850 μm is not less than 90% by weight;

(2) an elastic modulus index (EMI) of particles with a particle diameter of not less than 500 μm and less than 600 μm is not less than 5500; and (3) a recovery rate defined as Rec.CRC/CRC is 1.05 to 1.20.

The following description will discuss, in detail, physical properties of a particulate water absorbing agent in accordance with an embodiment of the present invention.

(2-1) Centrifuge Retention Capacity (CRC)

A particulate water absorbing agent in accordance with an embodiment of the present invention has a CRC of preferably not less than 23 g/g, more preferably not less than 25 g/g, even more preferably not less than 26 g/g. The upper limit value of CRC is preferably as high as possible, but is not limited to any particular value. The CRC is, however, preferably not more than 50 g/g, more preferably not more than 40 g/g, in terms of the balance between CRC and other physical properties.

The CRC for an embodiment of the present invention may thus be selected as appropriate from within the above range. The CRC is, for example, within the range of 23 g/g to 50 g/g, 23 g/g to 40 g/g, 25 g/g to 40 g/g, or 26 g/g to 50 g/g.

A CRC of not less than 23 g/g allows the particulate water absorbing agent to absorb a larger amount and thus be used suitably as an absorbent body for an absorbent article such as disposable diapers. A CRC of not more than g/g allows the particulate water absorbing agent to absorb, for example, a body fluid such as urine and blood at a higher speed and thus be used suitably in, for example, a disposable diaper having a high water absorption speed. The CRC may be controlled on the basis of, for example, an internal crosslinking agent and/or a surface-crosslinking agent.

(2-2) Fluid Retention Capacity Under Pressure (AAP)

A particulate water absorbing agent in accordance with an embodiment of the present invention has an AAP of preferably not less than 15 g/g, more preferably not less than 17 g/g, even more preferably not less than 20 g/g, especially even more preferably not less than 22 g/g, most preferably not less than 23 g/g. The upper limit value of AAP is preferably as high as possible, but is not limited to any particular value. The APP is, however, preferably not more than 30 g/g in terms of the balance between APP and other physical properties.

The AAP for an embodiment of the present invention may thus be selected as appropriate from within the above range. The AAP is, for example, within the range of 15 g/g to 30 g/g, 17 g/g to 30 g/g, 20 g/g to 30 g, or 23 g/g to 30 g/g.

An AAP of not less than 15 g/g is preferable because such an AAP reduces the re-wet, which a particulate water absorbing agent causes under pressure. The AAP may be controlled on the basis of, for example, the particle size and/or a surface-crosslinking agent.

(2-3) Water-Soluble Component (Ext)

A particulate water absorbing agent in accordance with an embodiment of the present invention has an Ext of normally not more than 50% by weight, preferably not more than 35% by weight, more preferably not more than 25% by weight, even more preferably not more than 15% by weight. The lower limit value of Ext is not limited to any particular value, but is preferably 0% by weight, more preferably approximately 0.1% by weight.

The Ext for an embodiment of the present invention may thus be selected as appropriate from within the above range. The Ext is, for example, within the range of 0% by weight to 50% by weight, 0% by weight to 25% by weight, 0.1% by weight to 35% by weight, or 0.1% by weight to 15% by weight.

An Ext of not more than 50% by weight allows the particulate water absorbing agent to have a high gel strength and excellent liquid permeability. Such a particulate water absorbing agent, in a case where it is used in an absorbent body for an absorbent article such as disposable diapers, has only a small re-wet when the absorbent body is pressurized. The Ext may be controlled on the basis of, for example, an internal crosslinking agent.

(2-4) Particle Size Distribution (PSD)

A particulate water absorbing agent in accordance with an embodiment of the present invention has a PSD in which the proportion of particles with a particle diameter of not less than 150 μm and less than 850 μm is not less than 90% by weight, preferably not less than 95% by weight, more preferably not less than 97% by weight, even more preferably 98% by weight (with an upper limit of 100% by weight). The proportion of particles with a particle diameter of not less than 150 μm and less than 710 μm is preferably not less than 90% by weight, more preferably not less than 95% by weight, even more preferably not less than 97% by weight, especially even more preferably 98% by weight (with an upper limit of 100 weight %).

More specifically, the proportion of particles with a particle diameter of not less than 150 μm and less than 300 μm is not less than 5% by weight, preferably not less than 7% by weight, more preferably not less than 10% by weight, further preferably 15% by weight (with an upper limit of 50% by weight). The proportion of particles with a particle diameter of not less than 300 μm and less than 425 μm is not less than 10% by weight, preferably not less than 12% by weight, more preferably not less than 15% by weight, further preferably 20% by weight (with an upper limit of 60% by weight). The proportion of particles with a particle diameter of not less than 425 μm and less than 500 μm is not less than 5% by weight, preferably not less than 7% by weight, more preferably not less than 10% by weight, further preferably 15% by weight (with an upper limit of 50% by weight). The proportion of particles with a particle diameter of not less than 500 µm and less than 600 µm is not less than 5% by weight, preferably not less than 7% by weight, more preferably not less than 10% by weight, further preferably 15% by weight (with an upper limit of 50% by weight). The proportion of particles with a particle diameter of not less than 600 µm and less than 850 µm is not less than 0.1% by weight, preferably not less than 0.3% by weight, more preferably not less than 0.5% by weight, further preferably 1% by weight (with an upper limit of 50% by weight). The total of the above proportions is preferably 90% by weight to 100% by weight, more preferably 95% by weight to 100% by weight.

The proportion of particles with a particle diameter of less than 150 µm is preferably not more than 5% by weight, more preferably not more than 4% by weight, even more preferably not more than 3% by weight. The expression "particles with a particle diameter of less than 150 µm" refers to a particulate water absorbing agent that passes through a JIS standard sieve (defined in JIS Z8801-1(2000)) having a mesh size of 150 µm.

The proportion of particles with a particle diameter of less than 150 µm is preferably not more than 5% by weight because such a proportion makes it possible to, during the production of a particulate water absorbing agent, reliably prevent a safety and sanitary problem of scattering of microparticles contained in the particulate water absorbing agent and to produce a particulate water absorbing agent having improved physical properties.

The proportion of particles with a particle diameter of not less than 850 µm is preferably not more than 5% by weight, more preferably not more than 3% by weight, even more preferably not more than 1% by weight.

The weight average particle diameter (D50) is set as appropriate within the range of preferably 200 µm to 600 µm, more preferably 300 µm to 500 µm, even more preferably 320 µm to 480 µm, especially even more preferably 340 µm to 460 µm.

A weight average particle diameter (D50) within the range of 200 µm to 600 µm makes it possible to produce a particulate water absorbing agent that has an excellent liquid permeability and water absorption speed. Using such a particulate water absorbing agent in an absorbent body for an absorbent article such as disposable diapers is preferable because the use makes it possible to prevent, for example, liquid leakage.

The logarithmic standard deviation (σζ) of a particle size distribution is set as appropriate within the range of preferably 0.20 to 0.50, more preferably 0.25 to 0.45, even more preferably 0.27 to 0.43, especially even more preferably 0.29 to 0.41.

A logarithmic standard deviation (σζ) of a particle size distribution within the range of 0.20 to 0.50 is preferable because such a σζ makes it possible to produce a particulate water absorbing agent that has an excellent liquid permeability and water absorption speed.

(2-5) Saline Flow Conductivity (SFC)

A particulate water absorbing agent in accordance with an embodiment of the present invention has an SFC of preferably not less than 10, more preferably not less than 20, even more preferably not less than 30, further even more preferably not less than 50, especially even more preferably not less than 70, most preferably not less than 90. The upper limit value of SFC is not limited to any particular value, but is preferably not more than 3000, more preferably not more than 2000.

The SFC for an embodiment of the present invention may thus be selected as appropriate from within the above range. The SFC is, for example, within the range of 10 to 3000, 30 to 3000, or 70 to 2000.

An SFC of not less than 10 is preferable because such an SFC makes it possible to produce a particulate water absorbing agent that has a high liquid permeability and that has a more excellent liquid absorption speed in a case where the particulate water absorbing agent is used in an absorbent body. The SFC has the unit "$\times 10^{-7} \cdot cm^3 \cdot s \cdot g^{-1}$".

(2-6) Free Swell Rate (FSR)

A particulate water absorbing agent in accordance with an embodiment of the present invention has an FSR of preferably not less than 0.28, more preferably not less than 0.30, even more preferably not less than 0.35. The upper limit value of FSR is preferably as high as possible, but is not limited to any particular value. The FSR is, however, preferably not more than 1.0 in terms of the balance between FSR and other physical properties.

The FSR for an embodiment of the present invention may thus be selected as appropriate from within the above range. The FSR is, for example, within the range of 0.28 to 1.0 or 0.35 to 1.0.

An FSR within the above range is preferable because a particulate water absorbing agent having such an FSR, in a case where the particulate water absorbing agent is used in an absorbent body, absorbs liquid more fully and causes no liquid leakage. The FSR has the unit "g/(g·s)".

(2-7) Vortex (Water Absorption Time)

A particulate water absorbing agent in accordance with an embodiment of the present invention has a Vortex of preferably not more than 42 seconds, more preferably not more than 40 seconds, even more preferably not more than 35 seconds, especially even more preferably not more than 30 seconds, most preferably not more than 25 seconds. The lower limit value of Vortex is not limited to any particular value as long as the value is more than 0, but is preferably not less than 5 seconds, more preferably not less than 10 seconds.

The Vortex for an embodiment of the present invention may thus be selected as appropriate from within the above range. The Vortex is, for example, more than 0 and not more than 42 seconds or within the range of 5 seconds to 40 seconds or 10 seconds to 30 seconds.

A Vortex of not more than 42 seconds is preferable because a particulate water absorbing agent having such a Vortex, in a case where the particulate water absorbing agent is used in an absorbent body, absorbs liquid more fully and causes no liquid leakage.

(2-8) Recovery CRC (Rec.CRC)

A particulate water absorbing agent in accordance with an embodiment of the present invention has a Rec.CRC of preferably not less than 24 g/g, more preferably not less than 26 g/g, even more preferably not less than 27 g/g. The upper limit value of Rec.CRC is preferably as high as possible, but is not limited to any particular value. The Rec.CRC is, however, preferably not more than 54 g/g, more preferably not more than 48 g/g, even more preferably not more than 47 g/g, especially even more preferably not more than 42 g/g, in terms of the balance between Rec.CRC and other physical properties.

The Rec.CRC for an embodiment of the present invention may thus be selected as appropriate from within the above range. The Rec.CRC is, for example, within the range of 24 g/g to 54 g/g, 26 g/g to 48 g/g, 27 g/g to 47 g/g, or 27 g/g to 42 g/g.

A Rec.CRC of not less than 24 g/g allows the particulate water absorbing agent to absorb a larger amount and thus be used suitably as an absorbent body for an absorbent article such as disposable diapers. A Rec.CRC of not more than 54 g/g allows the particulate water absorbing agent to absorb, for example, a body fluid such as urine and blood at a higher speed and thus be used suitably in, for example, a disposable diaper having a high water absorption speed.

(2-9) Recovery AAP (Rec.AAP)

A particulate water absorbing agent in accordance with an embodiment of the present invention has a Rec.AAP of preferably not less than 10 g/g, more preferably not less than 12 g/g, even more preferably not less than 15 g/g. The upper limit value of Rec.AAP is preferably as high as possible, but is not limited to any particular value. The Rec.AAP is, however, preferably not more than 30 g/g, more preferably not more than 25 g/g, in terms of the balance between Rec.AAP and other physical properties.

The Rec.AAP for an embodiment of the present invention may thus be selected as appropriate from within the above range. The Rec.AAP is, for example, within the range of 10 g/g to 30 g/g, 12 g/g to 30 g/g, 12 g/g to 25 g/g, or 15 g/g to 25 g/g.

A Rec.AAP of not less than 10 g/g is preferable because such an AAP, even after a particulate water absorbing agent has been swollen once, reduces the re-wet, which the particulate water absorbing agent causes under pressure.

(2-10) Recovery SFC (Rec.SFC)

A particulate water absorbing agent in accordance with an embodiment of the present invention has a Rec.SFC of preferably not less than 5, more preferably not less than 7, even more preferably not less than 8, especially even more preferably not less than 10.

A Rec.SFC of not less than 5 is preferable because such a Rec.SFC makes it possible to produce a particulate water absorbing agent that, even after the particulate water absorbing agent has been swollen once, has a high liquid permeability and that has a more excellent absorption speed in a case where the particulate water absorbing agent is used in an absorbent body. The Rec.SFC has the unit "$\times 10^{-7} \cdot cm^3 \cdot s \cdot g^{-1}$".

(2-11) Recovery Rate (Rec.CRC/CRC)

A particulate water absorbing agent in accordance with an embodiment of the present invention has a Rec.CRC/CRC of preferably not less than 1.05, more preferably not less than 1.06, even more preferably not less than 1.07, especially even more preferably not less than 1.08. The Rec.CRC/CRC has an upper limit value of preferably not more than 1.20, more preferably not more than 1.18, even more preferably not more than 1.16, especially even more preferably not more than 1.15.

The Rec.CRC/CRC for an embodiment of the present invention may thus be selected as appropriate from within the above range. The Rec.CRC/CRC is, for example, within the range of 1.05 to 1.20, 1.05 to 1.16, 1.06 to 1.16, or 1.08 to 1.15.

(2-12) Elastic Modulus Index (EMI)

A particulate water absorbing agent in accordance with an embodiment of the present invention has a high elasticity, a high recovery rate, an excellent water absorbing property, and an excellent liquid permeability. It is thus preferable that the elasticity is evaluated in terms of the elastic modulus. The elastic modulus is, however, known to vary according to the fluid retention capacity of the particulate water absorbing agent. It is thus preferable that the elasticity of a particulate water absorbing agent is expressed as an index that is set in view of the influence of the fluid retention capacity.

As described in the Examples section, the elastic modulus for an embodiment of the present invention is measured while swollen gel particles as a measurement target are sandwiched between the dish surface and the parallel plate surface of a rheometer and are under a load. If the swollen gel particles have a particle size distribution, swollen gel particles having larger particle diameters come into contact with the parallel plate surface first, and swollen gel particles having smaller particle diameters are thus not sandwiched. This problematically prevents the elastic modulus from being measured accurately.

In view of the above, the inventors of the present invention have discovered that the parameter "elastic modulus index (EMI)", which is obtained by correcting the elastic modulus on the basis of the fluid retention capacity of a particulate water absorbing agent and the theoretical surface area of swollen gel particles, is a value that accurately indicates the elasticity of a particulate water absorbing agent in accordance with an embodiment of the present invention and that correlates to the water absorption performance of the particulate water absorbing agent. The elastic modulus index (EMI) is determined as described in the Examples section.

As described above, if a particulate water absorbing agent in accordance with an embodiment of the present invention has a particle size distribution, the elastic modulus of the particulate water absorbing agent cannot be measured accurately. In view of that, an embodiment of the present invention is configured to first classify a particulate water absorbing agent as a measurement target into different particle diameter ranges and measure the elastic modulus for each particle size range to calculate the elastic modulus index (EMI).

The elastic modulus index (EMI) preferably has a high value for each particle size range as long as the recovery rate (Rec.CRC/CRC) is within the range of 1.05 to 1.20. This results in Rec.AAP and Rec.SFC being high as well. A particulate water absorbing agent of an embodiment of the present invention, in other words, maintains its properties such as water absorbing property and liquid permeability even after the particulate water absorbing agent has been swollen.

The following description will discuss preferable EMI ranges for each particle size range.

(2-12-1) EMI of Particles with a Particle Diameter of Not Less than 600 μm and Less than 710 μm The elastic modulus index (EMI) of particles with a particle diameter of not less than 600 μm and less than 710 μm as classified for the elastic modulus measurement is preferably not less than 5500, more preferably not less than 6000, even more preferably not less than 6500, especially even more preferably not less than 7000, most preferably not less than 7500. The EMI has an upper limit value of preferably not more than 15500, more preferably not more than 11500, even more preferably not more than 9500, especially even more preferably not more than 8500, most preferably not more than 8000.

(2-12-2) EMI of Particles with a Particle Diameter of Not Less than 500 μm and Less than 600 μm The elastic modulus index (EMI) of particles with a particle diameter of not less than 500 μm and less than 600 μm as classified for the elastic modulus measurement is not less than 5500, preferably not less than 6000, more preferably not less than 6500, even more preferably not less than 7000. The EMI has an upper limit value of preferably not more than 15000, more preferably not more than 11000, even more preferably not more than 9500, still even more preferably not more than 9000, especially even more preferably not more than 8000, most preferably not more than 7500.

(2-12-3) EMI of Particles with a Particle Diameter of Not Less than 425 μm and Less than 500 μm The elastic modulus index (EMI) of particles with a particle diameter of not less than 425 μm and less than 500 μm as classified for the elastic modulus measurement is preferably not less than 4500, more preferably not less than 5000, even more preferably not less than 5500, especially even more preferably not less than 6000, most preferably not less than 6500. The EMI has an upper limit value of preferably not more than 14500, more preferably not more than 10500, even more preferably not more than 8500, especially even more preferably not more than 7500, most preferably not more than 7000.

(2-12-4) EMI of Particles with a Particle Diameter of Not Less than 300 μm and Less than 425 μm The elastic modulus index (EMI) of particles with a particle diameter of not less than 300 μm and less than 425 μm as classified for the elastic modulus measurement is preferably not less than 3500, more preferably not less than 4000, even more preferably not less than 4500, especially even more preferably not less than 5000, most preferably not less than 6000. The EMI has an upper limit value of preferably not more than 14000, more preferably not more than 10000, even more preferably not more than 8000, especially even more preferably not more than 7000, most preferably not more than 6500.

(2-12-5) EMI of Particles with a Particle Diameter of Not Less than 150 μm and Less than 300 μm The elastic modulus index (EMI) of particles with a particle diameter of not less than 150 μm and less than 300 μm as classified for the elastic modulus measurement is preferably not less than 3500, more preferably not less than 4000. The EMI has an upper limit value of preferably not more than 13500, more preferably not more than 9500, even more preferably not more than 4500.

As described above, a particulate water absorbing agent in accordance with an embodiment of the present invention, in a case where (1) the proportion of particles with a particle diameter of not less than 150 μm and less than 850 μm is not less than 90% by weight, (2) the elastic modulus index (EMI) of particles with a particle diameter of not less than 500 μm and less than 600 μm is not less than 5500, and (3) Rec.CRC/CRC is within the range of 1.05 to 1.20, has physical properties that are only minimally degraded after the particulate water absorbing agent has been swollen with deionized water, and exhibits excellent physical properties such as a Rec.AAP of not less than 15 g/g and a Rec.SFC of not less than $5 \times 10^{-7} \cdot cm^3 \cdot s \cdot g^{-1}$.

A particulate water absorbing agent that satisfies only the requirements (1) and (3) or only the requirements (2) and (3) did not exhibit excellent values for both Rec.AAP and Rec.SFC.

(2-13) Diffusion Absorbency Period

A particulate water absorbing agent in accordance with an embodiment of the present invention has, under a load of 2.07 kPa, a first-time diffusion absorbency period of preferably not more than 26 seconds, more preferably not more than 24 seconds, a second-time diffusion absorbency period of preferably not more than 37 seconds, more preferably not more than 35 seconds, and a third-time diffusion absorbency period of preferably not more than 67 seconds, more preferably not more than 65 seconds. A particulate water absorbing agent in accordance with an embodiment of the present invention has, under a load of 6.21 kPa, a first-time diffusion absorbency period of preferably not more than 39 seconds, more preferably not more than 35 seconds, a second-time diffusion absorbency period of preferably not more than 75 seconds, more preferably not more than 70 seconds, and a third-time diffusion absorbency period of preferably not more than 160 seconds, more preferably not more than 140 seconds. Comparing diffusion absorbency periods makes it possible to evaluate the liquid absorption property under a high pressure. The comparison shows that in a case where the diffusion absorbency period is shorter, the particulate water absorbing agent exhibits a higher fluid retention capacity under pressure even after the particulate water absorbing agent has been swollen.

[3] Method for Producing Particulate Water Absorbing Agent

The following description will discuss a method for producing a particulate water absorbing agent of an embodiment of the present invention. The production method may be any method that allows the above-described particulate water absorbing agent to be produced, and is not limited to any particular method. A preferable example of the production method is a method including a polymerization step of polymerizing an aqueous monomer solution containing an acrylic acid (salt) as a main component to prepare a cross-linked hydrogel polymer. Such a production method makes it possible to efficiently produce a particulate water absorbing agent having physical properties described above.

(3-1) Step of Preparing Aqueous Monomer Solution

This step is a step of preparing an aqueous solution containing an acrylic acid (salt) as a main component (hereinafter referred to as an "aqueous monomer solution"). The aqueous monomer solution may contain a monomer slurry liquid to the extent that a particulate water absorbing agent to be produced will not have degraded water absorption performance. For convenience of description, however, this section describes an aqueous monomer solution.

The term "main component" means that the acrylic acid (salt) is used (contained) in an amount of normally not less than 50 mol %, preferably not less than 70 mol %, more preferably not less than 90 mol % (with an upper limit of 100 mol %), relative to the total amount of monomers used for a polymerization reaction (excluding an internal crosslinking agent).

(Acrylic Acid (Salt))

For an embodiment of the present invention, it is preferable that an acrylic acid and/or an acrylic acid salt (hereinafter referred to as "acrylic acid (salt)") is used as a monomer from the viewpoint of physical properties of a particulate water absorbing agent to be produced and productivity.

The acrylic acid is a publicly known acrylic acid. Such a publicly known acrylic acid is obtained by collecting, with use of a solvent such as water, a gaseous acrylic acid produced by catalytic gas-phase oxidation and then purifying the gaseous acrylic acid by distillation and/or crystallization. The publicly known acrylic acid contains a trace component(s) such as a polymerization inhibitor and an impurity.

The polymerization inhibitor is not limited to any particular one, but is preferably a methoxyphenol, more preferably p-methoxyphenol. The polymerization inhibitor is contained in the acrylic acid at a concentration that is set as appropriate at preferably not more than 200 ppm, more preferably within a range of 10 ppm to 160 ppm, even more preferably within a range of 20 ppm to 100 ppm, from the viewpoint of, for example, polymerizability of the acrylic acid and the color of a particulate water absorbing agent to be produced.

The impurity is not limited to any particular one, but may be an organic compound such as acetic acid, propionic acid, and furfural or an impurity contained in an acrylic acid disclosed in U.S. Patent Application Publication No. 2008/0161512.

The acrylic acid salt is produced by neutralizing the above acrylic acid with a basic compound below. The acrylic acid salt may be a commercially available acrylic acid salt (for example, sodium acrylate) or may be produced by neutralizing an acrylic acid in a plant for producing a particulate water absorbing agent.

(Basic Compound)

The term "basic compound" as used for an embodiment of the present invention refers to a compound that exhibits basicity such as sodium hydroxide. Commercially available sodium hydroxide, for example, contains a heavy metal such as zinc, iron, and/or lead as an impurity on the order of ppm, and may thus be technically referred to as "basic composition". An embodiment of the present invention, however, encompasses commercially available sodium hydroxide within the category of basic compounds.

Specific examples of the basic compound include a carbonate or bicarbonate of an alkali metal, a hydroxide of an alkali metal, ammonia, and organic amine. The basic compound is, among others, preferably a strongly basic compound from the viewpoint of physical properties of a particulate water absorbing agent to be produced. Specifically, the basic compound is preferably a hydroxide of an alkali metal such as sodium hydroxide, potassium hydroxide, and lithium hydroxide, more preferably sodium hydroxide. The basic compound is preferably in the form of an aqueous solution from the viewpoint of handleability.

(Neutralization)

In a case where the acrylic acid salt is produced by neutralizing an acrylic acid in a plant for producing a particulate water absorbing agent, the time point at which the neutralization is carried out is not limited to any particular one. The neutralization may be carried out with respect to an acrylic acid (that is, before the polymerization), the acrylic acid during crosslinking polymerization (during the polymerization), and/or a crosslinked hydrogel polymer produced through the crosslinking polymerization of the acrylic acid (after the polymerization). The neutralization is not limited to any particular type, and may be of a continuous type or a batch type. Of these two, a continuous type is preferable from the viewpoint of, for example, production efficiency.

In a case where an embodiment of the present invention uses an acrylic acid (salt), the neutralization rate is not limited to any particular value. The neutralization rate is set as appropriate within a range of preferably 10 mol % to 100 mol %, more preferably 30 mol % to 95 mol %, even more preferably 45 mol % to 90 mol %, especially even more preferably 60 mol % to 80 mol %, relative to the acid group of the monomer. Setting the neutralization rate within the above range prevents the particulate water absorbing agent from having a decreased fluid retention capacity and thus makes it possible to produce a particulate water absorbing agent having a high fluid retention capacity under pressure.

The preferable ranges of the neutralization rate are applied to any of the time period before the polymerization, the time period during the polymerization, and the time period after the polymerization. The preferable ranges are applied similarly to a particulate water absorbing agent as a finished product. With regard to neutralization conditions such as a neutralization apparatus, a neutralization temperature, and a retention time, the conditions disclosed in International Publication No. 2009/123197 and U.S. Patent Application Publication No. 2008/0194863 may be applied to an embodiment of the present invention.

(Other Monomer(s))

For an embodiment of the present invention, the above-described acrylic acid (salt) may be used in combination with, according to need, the monomer(s) (hereinafter referred to as "other monomer(s)") disclosed in U.S. Patent Application Publication No. 2005/0215734. The other monomer(s) is not limited to any particular one, and is, for example, a water-soluble or hydrophobic unsaturated monomer.

In a case where the other monomer(s) is used in combination, the other monomer(s) is used in an amount that is set as appropriate at preferably not more than 30 mol %, more preferably not more than 10 mol %, relative to the total amount of the monomers.

(Internal Crosslinking Agent)

The internal crosslinking agent for an embodiment of the present invention is one of the internal crosslinking agents disclosed in U.S. Pat. No. 6,241,928. One or more internal crosslinking agents are selected from the internal crosslinking agents in view of reactivity.

From the viewpoint of, for example, the water absorption performance of a particulate water absorbing agent to be produced, the internal crosslinking agent is preferably a compound having two or more polymerizable unsaturated groups, more preferably a compound that is pyrolytic at a drying temperature below, even more preferably a compound having a (poly)alkylene glycol structural unit and two or more polymerizable unsaturated groups.

The polymerizable unsaturated groups are not limited to any particular ones, but are preferably an allyl group or a (meth)acrylate group, more preferably a (meth)acrylate group. The (poly)alkylene glycol structural unit is not limited to any particular one, but is preferably polyethylene glycol. The n number is selected as appropriate from a range of preferably 2 to 100, more preferably 6 to 50.

The internal crosslinking agent is preferably water-soluble, and has a solubility of preferably not less than 0.1 g, more preferably not less than 1 g, relative to 100 g of water at 25° C.

The internal crosslinking agent for use in an embodiment of the present invention is thus preferably (poly)alkylene glycol di(meth)acrylate or (poly)alkylene glycol tri(meth) acrylate, more preferably (poly)ethylene glycol di(meth) acrylate.

The internal crosslinking agent is used in an amount that is set as appropriate within a range of preferably 0.001 mol % to 5 mol %, more preferably 0.002 mol % to 2 mol %, even more preferably 0.04 mol % to 1 mol %, especially even more preferably 0.06 mol % to 0.5 mol %, most preferably 0.07 mol % to 0.2 mol %, relative to the total amount of the monomers.

Using the internal crosslinking agent in an amount within the above range makes it possible to produce a desired particulate water absorbing agent. Using the internal crosslinking agent in an amount of less than 0.001 mol % is not preferable because such an amount tends to decrease the gel strength and increase the water-soluble component. Using the internal crosslinking agent in an amount of more than 5 mol % is not preferable because such an amount tends to decrease the fluid retention capacity.

For an embodiment of the present invention, the following method is preferably used: An aqueous monomer solution to which a certain amount of internal crosslinking agent has been added in advance is prepared. Then, the aqueous monomer solution is simultaneously subjected to polymerization and to a crosslinking reaction. Alternatively, other than the above method, examples of a possible method include a method in which an internal crosslinking agent is added during or after the polymerization so that postcrosslinking is carried out, a method in which radical crosslinking is carried out with use of a radical polymerization initiator, and a method in which radiation crosslinking is carried out with use of active energy rays such as an electron ray and an ultraviolet ray. Alternatively, these methods may be used in combination.

(Other Substances Added to Aqueous Monomer Solution)

An embodiment of the present invention may include adding any substance below to the aqueous monomer solution during the preparation thereof from the viewpoint of improved physical properties for a particulate water absorbing agent to be produced.

Specifically, a hydrophilic polymer such as starch, a starch derivative, cellulose, a cellulose derivative, polyvinyl alcohol, polyacrylic acid (salt), and crosslinked polyacrylic acid (salt) can be added in an amount of preferably not more than 50 weight %, more preferably not more than 20 weight %, even more preferably not more than 10 weight %, especially even more preferably not more than 5 weight % (with a lower limit of 0 weight %). A carbonate, an azo compound, a foaming agent for air bubbles or the like, a surfactant, a chain transfer agent, and/or the like can be added in an amount of preferably not more than 5 weight %, more preferably not more than 1 weight %, even more preferably not more than 0.5 weight % (with a lower limit of 0 weight %).

An embodiment of the present invention may include adding preferably a chelating agent, an α-hydroxycarboxylic acid compound, or an inorganic reducing agent, more preferably a chelating agent, during the preparation of the aqueous monomer solution from the viewpoint of color stability of a particulate water absorbing agent to be produced (that is, color stability of a particulate water absorbing agent that has undergone long-term storage under high temperature and high humidity) or urine resistance (prevention of gel deterioration).

The chelating agent and the like are each used in an amount that is set as appropriate within a range of preferably 10 ppm to 5000 ppm, more preferably 10 ppm to 1000 ppm, even more preferably 50 ppm to 1000 ppm, especially even more preferably 100 ppm to 1000 ppm, relative to the particulate water absorbing agent.

The chelating agent for an embodiment of the present invention is specifically one of the chelating agents disclosed in U.S. Pat. No. 6,599,989 and International Publication No. 2008/090961. The chelating agent is, among others, preferably an aminocarboxylic acid-based metal chelating agent or a polyvalent phosphoric acid-based compound.

The above substances are not necessarily be added to the aqueous monomer solution, but can be added during the polymerization, or can be added both to the aqueous monomer solution and during the polymerization.

In a case where the water-soluble resin or a water-absorbing resin is used as the hydrophilic polymer, a graft polymer or a water-absorbing resin composition (for example, a polymer produced from starch and an acrylic acid or a polymer produced from PVA and an acrylic acid) can be obtained. These polymers and water-absorbing resin compositions are also encompassed in the scope of the present invention.

(Monomer Component Concentration)

The above various substances are added during the step of preparing the aqueous monomer solution. The aqueous monomer solution may contain a monomer component at any concentration. The concentration is, however, set as appropriate within a range of preferably 10% by weight to 80% by weight, more preferably 20% by weight to 75% by weight, even more preferably 30% by weight to 70% by weight, especially even more preferably 40% by weight to 60% by weight, from the viewpoint of physical properties of a particulate water absorbing agent to be produced.

In a case where the form of polymerization used is aqueous solution polymerization or reversed phase suspension polymerization, a solvent other than water can be used in combination as necessary. In such a case, the type of the solvent used is not limited to any particular one.

The "monomer component concentration" is a value determined by Formula (1) below. The weight of the aqueous monomer solution does not include the weight of a graft component, water-absorbing resin, or a hydrophobic solvent used in reversed phase suspension polymerization.

[Math. 1]

$$\text{(Concentration of monomer component (weight \%))} = \text{(Weight of monomer component)}/\text{(Weight of aqueous monomer solution)} \times 100 \quad \text{(Formula 1)}$$

(3-2) Polymerization Step

This step is a step of polymerizing the aqueous monomer solution containing an acrylic acid (salt) as a main component, which aqueous monomer solution is prepared through the above step of preparing an aqueous monomer solution, to prepare a crosslinked hydrogel polymer (hereinafter referred to as "hydrogel").

The polymerization step may involve use of a radical polymerization initiator such as potassium persulfate, ammonium persulfate, sodium persulfate, t-butyl hydroperoxide, hydrogen peroxide, 2,2'-azobis(2-amidinopropane) dihydrochloride and/or active energy rays such as an electron ray and an ultraviolet ray.

In a case where the polymerization step involves use of a radical polymerization initiator, the polymerization step may involve combinational use of a reducing agent such as sodium sulfite, sodium hydrogen sulfite, ferrous sulfate, and L-ascorbic acid for a redox polymerization. The radical polymerization initiator is, however, preferably a pyrolytic radical initiator selected from azo compounds and/or peroxides, and is preferably a polymerization initiator that is water-soluble (that is, preferably not less than 1 g, more preferably not less than 10 g, of the polymerization initiator is dissolved in 100 g of water at 25° C.).

It is preferable that the radical initiator is added to the reaction system during the polymerization step. The "reaction system during the polymerization step" refers to a reaction system in which there is a possibility of polymerization of a water-soluble unsaturated monomer and generation of a hydrogel. Thus, the "reaction system during the polymerization step" may be any reaction system containing a water-soluble unsaturated monomer as a component, and may contain, for example, an internal crosslinking agent, a chain transfer agent, or α-hydroxycarboxylic acid (salt).

The radical polymerization initiator is added before the polymerization step and/or during the polymerization step, but not after the polymerization step.

The present specification uses the expression "before the polymerization step" to refer to a time period before the start of the polymerization of a monomer, the expression "during the polymerization step" to refer to a time period between the start of the polymerization of the monomer and the end of the polymerization, and the expression "after the polymerization step" to refer to a time period after the end of the polymerization of the monomer.

Whether the polymerization of the monomer has started can be determined on the basis of an increase in the temperature of a polymer which increase is caused by the polymerization. Specifically, a temperature increase of not lower than 3° C. (preferably not lower than 5° C.) allows for determination that the polymerization of the monomer has started.

Whether the polymerization of the monomer has ended can be determined on the basis of, for example, whether the temperature increase during the polymerization has reached its peak and the amount of residual monomer has become not more than 5% by weight.

The radical polymerization initiator (in particular, a pyrolytic radical initiator) is used in an amount that is set as appropriate within a range of preferably 0.051 mol % to 1.000 mol %, more preferably 0.054 mol % to 0.2000 mol %, even more preferably 0.058 mol % to 0.1000 mol %, relative to the entire monomer.

(Form of Polymerization)

The polymerization step of an embodiment of the present invention may involve bulk polymerization, reversed phase suspension polymerization, or precipitation polymerization. The polymerization step, however, preferably involves aqueous solution polymerization with use of an aqueous solution or aqueous dispersion of the monomer in view of, for example, performance and ease of control of the polymerization. Such a polymerization method is disclosed in, for example, U.S. Pat. Nos. 4,625,001, 4,769,427, 4,873,299, 4,093,776, 4,367,323, 4,446,261, 4,683,274, 4,690,996, 4,721,647, 4,738,867, and U.S. Pat. No. 4,748,076, and U.S. Patent Application No. 2002/40095.

As described above, the polymerization step for an embodiment of the present invention may involve spray droplet polymerization or reversed phase suspension polymerization to prepare a particulate hydrogel. It is, however, desirable that the polymerization step involves aqueous solution polymerization from the viewpoint of, for example, the liquid permeability (SFC) and water absorption speed (FSR) of a particulate water absorbing agent to be produced and ease of control of polymerization.

The aqueous solution polymerization can be tank-type (silo-type) unstirring polymerization. However, the aqueous solution polymerization is preferably kneader polymerization or belt polymerization, more preferably continuous aqueous solution polymerization, even more preferably high-concentration continuous aqueous solution polymerization, especially even more preferably high-concentration high-temperature starting continuous aqueous solution polymerization.

Stirring polymerization means polymerizing hydrogel while stirring the hydrogel, particularly polymerizing hydrogel while stirring and grain-refining the hydrogel (wherein the hydrogel is preferably a hydrogel having a polymerization rate of not less than 10 mol %, more preferably a hydrogel having a polymerization rate of not less than 50 mol %). An aqueous monomer solution (having a polymerization rate within a range of 0 mol % to less than 10 mol %) can be stirred as appropriate before and/or after the unstirring polymerization is carried out.

Examples of the continuous aqueous solution polymerization include continuous kneader polymerization (disclosed in U.S. Pat. Nos. 6,987,171 and 6,710,141, and others), and continuous belt polymerization (disclosed in U.S. Pat. Nos. 4,893,999 and 6,241,928, U.S. Patent Application Publication No. 2005/215734, and others). These aqueous solution polymerizations can produce a particulate water absorbing agent with high productivity.

In high-concentration continuous aqueous solution polymerization, the monomer concentration (solid content) is set as appropriate at preferably not less than 35 weight %, more preferably not less than 40 weight %, even more preferably not less than 45 weight % (but not more than the saturated concentration). In high-temperature starting continuous aqueous solution polymerization, the polymerization starting temperature is set as appropriate at preferably not lower than 30° C., more preferably not lower than 35° C., even more preferably not lower than 40° C., especially even more preferably not lower than 50° C. (but not higher than the boiling temperature). The high-concentration high-temperature starting continuous aqueous solution polymerization is a combination of the high-concentration continuous aqueous solution polymerization and the high-temperature starting continuous aqueous solution polymerization.

The high-concentration high-temperature starting continuous aqueous solution polymerization is disclosed in U.S. Pat. Nos. 6,906,159 and 7,091,253, and others. The high-concentration high-temperature starting continuous aqueous solution polymerization is preferable because it can produce a particulate water absorbing agent with a high degree of whiteness and can be easily applied to industrial-scale production.

Therefore, the polymerization method used in the production method of an embodiment of the present invention is suitably applied to a large-scale production apparatus having a great production volume per production line. The production volume is set as appropriate at preferably not less than 0.5 t/hr, more preferably not less than 1 t/hr, even more preferably not less than 5 t/hr, especially even more preferably not less than 10 t/hr.

The polymerization can be carried out under air atmosphere. It is, however, preferable from the viewpoint of coloring prevention that the polymerization is carried out under inert gas atmosphere such as water vapor, nitrogen, or argon (with, for example, an oxygen concentration of not more than 1 volume %). It is further preferable that the polymerization is carried out after oxygen dissolved in a monomer(s) or in a solution containing a monomer(s) is substituted (deaerated) with inert gas (by, for example, less than 1 mg/L of oxygen). Such deaeration allows for a monomer(s) having an excellent stability, without causing gelling before polymerization. This makes it possible to provide a particulate water absorbing agent with better physical properties and a higher degree of whiteness.

The amount of inert gas to be used is set as appropriate within a range of preferably 0.005 weight % to 0.2 weight %, more preferably 0.01 weight % to 0.1 weight %, even more preferably 0.015 weight % to 0.5 weight %, relative to the total amount of the monomers. Further, nitrogen is preferably used as the inert gas.

In the polymerization step of an embodiment of the present invention, a surfactant and/or a dispersant can be used if necessary. The use of the surfactant and/or the dispersing agent allows gas bubbles to be stably suspended in a water-absorbing resin during the polymerization. Further, by adjusting the type(s) or amount(s) of the surfactant and/or the dispersant as appropriate, it is possible to produce a particulate water absorbing agent having intended physical properties. It is preferable that the surfactant is a non-polymeric surfactant and that the dispersant is a polymeric dispersant. Further, it is preferable that the surfactant and/or the dispersant is added before the aqueous monomer solution prior to or during the polymerization reaches a temperature of not lower than 50° C. The amount of the surfactant and/or the dispersant to be used can be determined as appropriate according to the type(s) of the surfactant and/or the dispersant.

The polymerization step may use, for example, a method of carrying out thin-layer polymerization involving use of an aqueous monomer solution containing a monomer at a high concentration (Method 1) and a method of carrying out foaming polymerization under reduced pressure (Method 2).

Regarding Method 1, carrying out thin-layer polymerization with use of a high-concentration aqueous monomer solution makes it easy to control the temperature, and to thereby render uniform the molecular weight of the cross-linked hydrogel polymer and more efficiently produce a particulate water absorbing agent having the above-described physical properties. The aqueous monomer solution contains a monomer at a concentration that is set as appropriate at preferably not less than 35% by weight, more preferably not less than 40% by weight, even more preferably not less than 45% by weight.

An example method of thin-layer polymerization is a method of sandwiching the aqueous monomer solution between glass plates and carrying out polymerization. In this case, the glass plates are separated from each other by a distance (that is, the thickness of the layer of the aqueous monomer solution) that is set as appropriate within a range of preferably 1 mm to 10 mm, more preferably 3 mm to 7 mm. The temperature at which the polymerization is carried out is set as appropriate within a range of preferably 40° C. to 70° C., more preferably 50° C. to 60° C.

Regarding Method 2, carrying out the polymerization step under reduced pressure makes it easy to remove heat during the polymerization, and to thereby render uniform the molecular weight of the polymer and more efficiently produce a particulate water absorbing agent having the above-described physical properties. In this case, it is preferable that the polymerization step is carried out inside a hermetically sealed container. The hermetically sealed container has an internal pressure that is set as appropriate at preferably not more than 95 kPa, more preferably not more than 90 kPa, even more preferably not more than 85 kPa, especially even more preferably not more than 80 kPa.

(3-3) Gel-Crushing Step

This step is an optional step of gel-crushing the hydrogel, prepared through the polymerization step, to obtain hydrogel in the form of particles (hereinafter referred to as "particulate hydrogel").

While the hydrogel prepared through the polymerization step may be dried without being processed in advance, the hydrogel is gel-crushed into particles according to need with use of a gel crusher (for example, a kneader, a meat chopper, or a cutter mill) during or after the polymerization.

International Publication No. 2011/126079 discloses conditions and the like that are suitably applicable to an embodiment of the present invention as a preferable form of the gel-crushing.

(3-4) Drying Step

This step is a step of drying the particulate hydrogel, prepared through the gel-crushing step, to a desired range of resin solid content so as to obtain a dry polymer.

The "resin solid content" is a value determined from a drying loss (that is, a change in the weight caused by heating 1 g of a sample at 180° C. for three hours). The resin solid content is preferably not less than 90% by weight, more preferably not less than 95% by weight.

This step may involve any drying method. Examples of the drying method include thermal drying, hot air drying, drying under reduced pressure, fluidized bed drying, infrared drying, microwave drying, drying with use of a drum dryer, drying by azeotropic dehydration with a hydrophobic organic solvent, and high humidity drying with use of high temperature water vapor. The drying method is, among others, preferably hot air drying, more preferably band drying (in which hot air drying is carried out on a through-flow belt), from the viewpoint of drying efficiency.

In a case where this step involves hot air drying, the amount of hot air is set as appropriate within a range of preferably 0.01 m/sec to 10 m/sec, more preferably 0.1 m/sec to 5 m/sec.

This step uses a drying temperature that is set as appropriate within a range of preferably 100° C. to 250° C., more preferably 130° C. to 220° C., even more preferably 150° C. to 200° C.

A drying temperature of not lower than 100° C. makes it possible to change the polymer chain in the water-absorbing resin and to thereby produce a particulate water absorbing agent having improved physical properties. A drying temperature of not higher than 250° C. makes it possible to reduce damage to the water-absorbing resin and to thereby prevent a particulate water absorbing agent to be produced from having an increased water-soluble content.

This step uses a drying time period that is set as appropriate within a range of preferably 10 minutes to 120 minutes, more preferably 20 minutes to 90 minutes, even more preferably 30 minutes to 60 minutes.

A drying time period of not less than 10 minutes makes it possible to change the polymer chain in the water-absorbing resin and to thereby produce a particulate water absorbing agent having improved physical properties. A drying time period of not more than 120 minutes makes it possible to reduce damage to the water-absorbing resin and to thereby prevent a particulate water absorbing agent to be produced from having an increased water-soluble content.

The drying temperature and drying time period depend on the surface area and moisture content of the particulate hydrogel and the kind of the dryer, and are selected as appropriate so that a particulate water absorbing agent to be produced will have a moisture content within a desired range. The drying temperature is defined by the temperature of the heat medium (for example, in the case of hot air drying, the temperature of the hot air). In a case where a method is used in which the drying temperature cannot be defined by the temperature of the heat medium as in the case of, for example, microwave drying, the drying temperature is defined by the temperature of the dried product. The drying temperature may be constant or changed as appropriate during the drying.

(3-5) Pulverizing Step and Classification Step

This step is a step of pulverizing the dry polymer, prepared through the drying step (pulverizing step), and adjusting the particle size of the pulverized polymer to a particle size within a desired range (classification step) so as to obtain water-absorbing resin powder. This step is carried out in such a manner that a particulate water absorbing agent to be produced will have a particle size distribution (PSD) within the range described in (2-4) above. This step differs from the gel-crushing step in (3-2) above in that a product to be pulverized has been subjected to the drying step.

The device (pulverizer) for use in pulverizing the dry polymer is not limited to any particular one. Examples of the device include a high-speed pulverizer such as a roll mill, a hammer mill, a screw mill, and a pin mill, a vibrating mill, a knuckle-type pulverizer, and a cylindrical mixer. These devices are used in combination according to need. Among the above, it is preferable to use a roll mill from the viewpoint of control of particle size distribution.

The particle size after the pulverization may be adjusted (classified) by any method. Examples of the method include sieve classification with use of a JIS standard sieve (JIS Z8801-1 (2000)) and airflow classification.

(3-6) Surface-Crosslinking Step

This step is a step of forming a portion with a higher crosslinking density in a surface layer (that is, a portion of the water-absorbing resin powder which portion is up to several tens of micrometers deep from the surface) of the water-absorbing resin powder produced through the above steps. This step includes a mixing step, a heat treatment step, and optionally a cooling step. The surface-crosslinking step involves, for example, radical cross-linking at the surface of the water-absorbing resin powder, surface polymerization of the water-absorbing resin powder, and a crosslinking reaction with a surface-crosslinking agent so as to produce surface-crosslinked water-absorbing resin powder (hereinafter referred to as "water-absorbing resin particles").

Typically, surface-crosslinked water-absorbing resin has only a small re-wet when it is pressurized after being swollen, and makes it possible to improve, for example, the AAP and SFC.

The above applies similarly to a particulate water absorbing agent in accordance with an embodiment of the present invention. In a case where the particulate water absorbing agent is used in an absorbent body for an absorbent article, the particulate water absorbing agent preferably has only a small re-wet when the particulate water absorbing agent is pressurized, and makes it possible to produce an absorbent body having an excellent liquid absorption speed.

(Covalent Bonding Surface-Crosslinking Agent)

A surface-crosslinking agent used in an embodiment of the present invention is not limited to any particular one. Examples of the surface-crosslinking agent include an organic surface-crosslinking agent and an inorganic surface-crosslinking agent. Among others, an organic surface-crosslinking agent (dehydrating and condensing surface-crosslinking agent) that is reactive with a carboxyl group is preferable, from the viewpoint of physical properties of a particulate water absorbing agent to be produced and handleability of the surface-crosslinking agent. For example, one of the surface-crosslinking agents disclosed in U.S. Pat. No. 7,183,456 can be used, or two or more of the surface-crosslinking agents disclosed in U.S. Pat. No. 7,183, 456 can be used. Specifically, examples of the surface-crosslinking agent include a polyhydric alcohol compound, an epoxy compound, a haloepoxy compound, a polyamine compound, a condensed product with a haloepoxy compound of the polyamine compound, an oxazoline compound, an oxazolidinone compound, an alkylene carbonate compound, and a cyclic urea compound. Among others, from the viewpoint of the effect of an embodiment of the present invention, it is preferable to use at least one dehydration esterification surface-crosslinking agent selected from among a polyhydric alcohol compound, an alkylene carbonate compound, and an oxazolidinone compound.

The amount of such a surface-crosslinking agent used (or the total amount used in a case where a plurality of surface-crosslinking agents are used) is set as appropriate within a range of preferably 0.001 parts by weight to 10 parts by weight, more preferably 0.01 parts by weight to 5 parts by weight, relative to 100 parts by weight of the water-absorbing resin powder.

The surface-crosslinking agent is preferably added in the form of an aqueous solution to the water-absorbing resin powder. In this case, the amount of water used is set as appropriate within a range of preferably 0.1 parts by weight to 20 parts by weight, more preferably 0.5 parts by weight to 10 parts by weight, relative to 100 parts by weight of the water-absorbing resin powder. Further, a hydrophilic organic solvent may be used in combination according to need. In this case, the amount of the hydrophilic organic solvent used is set as appropriate at preferably not more than 10 parts by weight, more preferably not more than 5 parts by weight, relative to 100 parts by weight of the water-absorbing resin powder. Examples of the hydrophilic organic solvent include a lower alcohol such as methyl alcohol; a ketone such as acetone; an ether such as dioxane; an amide such as N,N-dimethylformamide; a sulfoxide such as dimethyl sulfoxide; and a polyhydric alcohol such as ethylene glycol.

A polyhydric metal salt added during a polyhydric metal salt adding step described later may be mixed with the surface-crosslinking agent (aqueous solution) in an amount of preferably not more than 5 parts by weight relative to 100 parts by weight of the water-absorbing resin powder or may be added in a separate mixing step.

(Mixing Step)

This step is a step of mixing the water-absorbing resin powder and the surface-crosslinking agent with each other to obtain a humidified mixture. The method of mixing the water-absorbing resin powder and the surface-crosslinking agent with each other is not limited to any particular one, and can be, for example, a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

An apparatus for the above mixing is not limited to any particular one. The apparatus is preferably a high-speed stirring mixer, more preferably a high-speed stirring continuous mixer. The rotation rate of the mixer is set as appropriate within a range of preferably 100 rpm to 10000 rpm, more preferably 300 rpm to 2000 rpm. Further, the residence time for which the humidified mixture resides in the mixer is set as appropriate preferably within 180 seconds, more preferably within a range of 0.1 seconds to 60 seconds, even more preferably within a range of 1 second to 30 seconds.

(Heat Treatment Step)

This step is a step of heating the humidified mixture, which has been obtained in the mixing step, so as to cause cross-linking reaction on the surface of the water-absorbing resin powder.

An apparatus for performing the cross-linking reaction is not limited to any particular one, and can be preferably a paddle dryer. The heating temperature in heat treatment during the crosslinking reaction is set as appropriate depending on the type of the surface-crosslinking agent in use. The heating temperature is set as appropriate within a range of preferably 40° C. to 250° C., more preferably 150° C. to 250° C.

A heat-treatment temperature of not lower than 40° C. makes it possible to further improve water absorbent properties such as AAP and SFC. A heat-treatment temperature of not higher than 250° C. makes it possible to prevent degradation of the water-absorbing resin powder and a decrease in physical properties caused by the degradation.

The heat treatment during the crosslinking reaction is carried out for a time period that is set as appropriate within a range of preferably 1 minute to 2 hours, more preferably 5 minutes to 1 hour.

(Cooling Step)

This step is an optional step which is carried out after the heat treatment step according to need. In this step, the mixture having undergone the heat treatment is forcibly cooled to a predetermined temperature.

An apparatus for carrying out the cooling is not limited to any particular one. The apparatus, however, preferably has specifications identical to those of the apparatus used during the heat treatment step, more preferably a paddle dryer. This is because such an apparatus can be used as a cooling apparatus by replacing a heat medium with a refrigerant. Note that in this cooling step, the mixture having undergone the heat treatment is forcibly cooled according to need to a temperature within a range of preferably 40° C. to 80° C., more preferably 50° C. to 70° C. In a case where the classification step (referred to also as "sizing step") is carried out after the cooling step, the cooling is preferably carried out in such a manner as to satisfy the conditions described above for the classification step. The mixture having undergone the heat treatment is referred to as "water-absorbing resin particles" for convenience.

(Other Surface-Crosslinking)

It is possible to use, instead of a method in which the surface-crosslinking agent is used, a surface-crosslinking method in which a radical polymerization initiator is used (U.S. Pat. No. 4,783,510, and International Publication No. 2006/062258), or a surface-crosslinking method in which a monomer(s) is polymerized on a surface of water-absorbing resin (U.S. Patent Application Publication Nos. 2005/048221 and 2009/0239966, and International Publication No. 2009/048160).

(3-7) Polyhydric Metal Salt Adding Step

This step is a step of adding a polyhydric metal salt to the water-absorbing resin particles obtained through the surface-crosslinking step. This step is preferably carried out during the surface-crosslinking or after the surface-crosslinking. Adding a polyhydric metal salt, preferably a trivalent water-soluble polyhydric metal salt, to the water-absorbing resin particles is preferable because the addition makes it possible to produce a particulate water absorbing agent with an improved SFC without greatly decreasing the AAP.

The polyhydric metal salt is preferably added in the form of an aqueous solution. In that case, the polyhydric metal salt is contained in the aqueous solution at a concentration that is set as appropriate at preferably not less than 50%, more preferably not less than 60%, even more preferably not less than 70%, especially even more preferably not less than 80%, most preferably not less than 90% (but not more than the saturated concentration), relative to the saturation concentration in order to reduce permeation of the polyhydric metal salt into the water-absorbing resin and diffusion thereof in the water-absorbing resin.

The aqueous solution of the polyhydric metal salt may further contain the above-described hydrophilic organic solvent and/or an organic acid such as lactic acid or a salt thereof. This is preferable because it reduces at least permeation of the polyhydric metal salt into the water-absorbing resin and diffusion thereof in the water-absorbing resin and improves the mixing property.

Examples of the polyhydric metal salt for use in this step include a sulfate, a nitrate, a carbonate, a phosphate, an organic salt, and a halide (such as a chloride) of a metal selected from, for example, Zn, Be, Mg, Ca, Sr, Al, Fe, Mn, Ti, Zr, Ce, Ru, Y, and Cr. An embodiment of the present invention may also use a polyhydric metal salt disclosed in Japanese Patent Application Publication, Tokukai, No. 2005-11317.

Among the above polyhydric metal salts, it is most preferable to use a trivalent water-soluble polyhydric metal salt. Examples of the trivalent water-soluble polyhydric metal salt include aluminum chloride, polyaluminum chloride, aluminum sulfate, aluminum nitrate, aluminum potassium sulfate, aluminum sodium sulfate, potassium alum, ammonium alum, sodium alum, sodium aluminate, iron (III) chloride, cerium (III) chloride, ruthenium (III) chloride, yttrium (III) chloride, and chromium (III) chloride.

It is preferable to use a salt containing water of crystallization from the viewpoint of solubility of liquid to be absorbed such as urine. It is preferable to use, among others, an aluminum compound such as aluminum chloride, polyaluminum chloride, aluminum sulfate, aluminum nitrate, bis aluminum potassium sulfate, bis aluminum sodium sulfate, potassium alum, ammonium alum, sodium alum, and sodium aluminate, more preferably aluminum sulfate, even more preferably an aqueous solution of aluminum sulfate. In a case where an aqueous aluminum sulfate solution is used, the aluminum sulfate has a concentration of most preferably not less than 90% of the saturation concentration. An embodiment of the present invention may use only one of the above or two or more of the above in combination.

The polyhydric metal salt is added in an amount that is set as appropriate within a range of preferably 0.001% by weight to 5% by weight, more preferably 0.01% by weight to 1% by weight, relative to 100 parts by weight of the water-absorbing resin particles.

[4] Applications of Particulate Water Absorbing Agent

Applications of a particulate water absorbing agent in accordance with an embodiment of the present invention are not limited to any particular ones. However, the particulate water absorbing agent is preferably used as, for example, an absorbent body for an absorbent article such as disposable diapers, sanitary napkins, and incontinence pads. The particulate water absorbing agent shows an excellent performance in a case where it is used in, among others, high-concentration diapers (disposable diapers each of which contains a large amount of water-absorbing resin).

The term "absorbent body" refers to a constituent element of the above absorbent article which constituent element contains at least a particulate water absorbing agent in accordance with an embodiment of the present invention and optionally contains another absorbent material(s) (for example, fibrous substance such as pulp fiber).

The absorbent article contains an absorbent body having a water-absorbing resin content (core concentration, that is, the content of a particulate water absorbing agent relative to the combined amount of the particulate water absorbing agent and the fibrous material) that is set as appropriate within a range of preferably 30 weight % to 100 weight %, more preferably 40 weight % to 100 weight %, even more preferably 50 weight % to 100 weight %, further even more preferably 60 weight % to 100 weight %, especially even more preferably 70 weight % to 100 weight %, most preferably 75 weight % to 95 weight %.

[5] Modes of the Present Invention

Specifically, the present invention may be in any of the modes below.

1. A particulate water absorbing agent having a polyacrylic acid (salt)-based water-absorbing resin as a main component, being surface-crosslinked and satisfying physical properties (1) to (3) below:

(1) a proportion of particles with a particle diameter of not less than 150 μm and less than 850 μm is not less than 90% by weight;

(2) an elastic modulus index (EMI) of particles with a particle diameter of not less than 500 μm and less than 600 μm is not less than 5500; and (3) a recovery rate defined as Rec.CRC/CRC is 1.05 to 1.20.

2. The particulate water absorbing agent according to 1, wherein said recovery rate in (3) above is 1.05 to 1.16.

3. The particulate water absorbing agent according to 1 or 2, wherein said elastic modulus index (EMI) in (2) above is 6000 to 9500.

4. The particulate water absorbing agent according to any one of 1 to 3, wherein a fluid retention capacity under pressure (AAP) is not less than 20 g/g.

5. The particulate water absorbing agent according to any one of 1 to 4, wherein a saline flow conductivity (SFC) is not less than $10 \times 10^{-7} \cdot cm^3 \cdot s \cdot g^{-1}$.

6. The particulate water absorbing agent according to any one of 1 to 5, wherein a water absorption time according to a vortex method is not more than 42 seconds.

7. The particulate water absorbing agent according to any one of 1 to 6, wherein a free swell rate (FSR) is not less than 0.28 g/(g·s).

8. The particulate water absorbing agent according to any one of 1 to 7, wherein the particulate water absorbing agent is surface-crosslinked by a covalent bonding surface-crosslinking agent.

9. The particulate water absorbing agent according to any one of 1 to 8, wherein a proportion of particles with a particle diameter of less than 150 μm is not more than 5% by weight.

10. The particulate water absorbing agent according to any one of 1 to 9, further satisfying a physical property (4) below:

(4) an elastic modulus index (EMI) of particles with a particle diameter of not less than 425 μm and less than 500 μm is not less than 4500.

11. The particulate water absorbing agent according to 10, further satisfying a physical property (5) below:

(5) an elastic modulus index (EMI) of particles with a particle diameter of not less than 300 μm and less than 425 μm is not less than 3500.

12. The particulate water absorbing agent according to any one of 1 to 11, having:

(a) a proportion of particles with a particle diameter of not less than 150 μm and less than 300 μm being 5% by weight to 50% by weight;

(b) a proportion of particles with a particle diameter of not less than 300 μm and less than 425 μm being 10% by weight to 60% by weight;

(c) a proportion of particles with a particle diameter of not less than 425 μm and less than 500 μm being 5% by weight to 50% by weight;

(d) a proportion of particles with a particle diameter of not less than 500 μm and less than 600 μm being 5% by weight to 50% by weight; and (e) a proportion of particles with a particle diameter of not less than 600 μm and less than 850 μm being 0.1% by weight to 50% by weight, wherein a sum of the proportions of the particles having the particle diameters each defined in (a) to (e) above is 90% by weight to 100% by weight.

13. The particulate water absorbing agent according to any one of 1 to 12, wherein a weight average particle diameter (D50) is 300 μm to 500 μm and a logarithmic standard deviation (σζ) is 0.25 to 0.45.

14. An absorbent body, including a particulate water absorbing agent according to any one of 1 to 13.

15. An absorbent article, including a particulate water absorbing agent according to any one of 1 to 13.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will discuss an embodiment of the present invention with reference to Examples. It should be noted that the present invention is not limited in construction to the Examples. Unless otherwise stated, physical properties specified in the claims or Examples of the present application were obtained by EDANA methods and other measurement methods below under conditions where the temperature was room temperature (20° C. to 25° C.) and the humidity was 50 RH %.

For electric devices used in the Examples and Comparative Examples, power sources of 200 V or 100 V and 60 Hz were used. For convenience, "liter" may be referred to as "L", and "weight %" may be referred to as "wt %". Further, deionized water used in, for example, measurement of physical properties of a particulate water absorbing agent and Examples was of ISO03696 Grade 2 unless otherwise specified.

[Measurement of Physical Properties of Particulate Water Absorbing Agent]

The following description will discuss methods for measuring physical properties of a particulate water absorbing agent in accordance with an embodiment of the present invention. In a case where the measurement target is something other than a particulate water absorbing agent, for example, water-absorbing resin powder, the term "particulate water absorbing agent" in the description of the physical property measurement is construed as meaning water-absorbing resin powder.

(1) Centrifuge Retention Capacity (CRC)

The CRC of a particulate water absorbing agent in accordance with an embodiment of the present invention was measured in conformity with an EDANA method (ERT 441.2-02).

(2) Fluid Retention Capacity Under Pressure (AAP)

The AAP of a particulate water absorbing agent in accordance with an embodiment of the present invention was measured in conformity with an EDANA method (ERT 442.2-02) with use of a device (see FIG. 1). The measurement was carried out under a load changed to 4.83 kPa (0.7 psi).

(3) Water-Soluble Component (Ext)

The Ext of a particulate water absorbing agent in accordance with an embodiment of the present invention was measured in conformity with an EDANA method (ERT 470.2-02).

(4) Particle Size Distribution (PSD), Weight Average Particle Diameter (D50), and Logarithmic Standard Deviation ($\sigma\zeta$) of Particle Size Distribution The PSD of a particulate water absorbing agent in accordance with an embodiment of the present invention was measured in conformity with an EDANA method (ERT 420.2-02). The D50 and the $\sigma\zeta$ were measured in conformity with "(3) Mass-Average Particle Diameter (D50) and Logarithmic Standard Deviation ($\sigma\zeta$) of Particle Diameter Distribution" of U.S. Pat. No. 7,638,570.

(5) Saline Flow Conductivity (SFC)

The SFC of a particulate water absorbing agent in accordance with an embodiment of the present invention was measured in conformity with a measurement method disclosed in U.S. Pat. No. 5,669,894 and with use of a device (see FIG. 2).

(6) Free Swell Rate (FSR)

The FSR of a particulate water absorbing agent in accordance with an embodiment of the present invention was measured in conformity with a measurement method disclosed in International Publication No. 2009/016055.

(7) Vortex (Water Absorption Time)

The Vortex of a particulate water absorbing agent in accordance with an embodiment of the present invention was measured through the procedure below.

First, 0.02 parts by weight of food blue No. 1 (CAS No. 3844-45-9) as a food additive was added to 1.000 part by weight of an aqueous sodium chloride solution (physiological saline) prepared in advance at 0.90 weight % to color the physiological saline blue. Then, the temperature of the physiological saline was adjusted to 30° C.

Next, 50 ml of the blue physiological saline was weighed out and put into a 100-ml beaker. While the physiological saline was being stirred at 600 rpm with use of a magnet stirrer that was made of Teflon (registered trademark) and that had a cylindrical shape with a length of 40 mm and a thickness of 8 mm, 2.0 g of particulate water absorbing agent was put into the physiological saline.

The starting point and ending point during measurement of a water absorption period were in conformity with a standard described in JIS K 7224 (1996) "Koukyusuiseijyushi no Kyusuisokudo Shiken Houhou Kaisetsu (Explanation of Method for Testing Absorption Speed of Superabsorbent Resin)".

(8) Recovery CRC (Rec.CRC)

The Rec.CRC of a particulate water absorbing agent in accordance with an embodiment of the present invention was measured through the procedure below.

First, 0.100 g of particulate water absorbing agent was weighed out and uniformly placed in a nonwoven fabric bag (80 mm×100 mm) made of the same material as that of a bag used for the measurement under "(1) CRC" above. The bag was heat-sealed. The bag was then immersed into deionized water having a temperature adjusted to 25° C.±3° C. After 90 minutes, the bag was pulled out and drained with use of a centrifuge (available from KOKUSAN Corporation, type H-122) at 250 G for 3 minutes.

Subsequently, the drained bag was immersed into 1000 ml of a 0.9 weight % aqueous sodium chloride solution having a temperature adjusted to 25° C.±3° C. After 1 hour, the bag was pulled out, and was immersed into 500 ml of another 0.9 weight % aqueous sodium chloride solution. This operation was repeated until the total immersion time period reached 3 hours. Then, the bag was pulled out and drained with use of the centrifuge at 250 G for 3 minutes. Subsequently, the weight W3 (g) of the bag was measured.

A similar operation was carried out without a particulate water absorbing agent, and the weight W4 (g) of the bag in that case was measured. The Rec.CRC was calculated in accordance with Formula 2 below.

[Math. 2]

$$\text{Rec.CRC (g/g)} = \{(W3-W4)/(\text{Weight of particulate water absorbing agent})\} - 1 \quad \text{(Formula 2)}$$

(9) Recovery AAP (Rec.AAP)

The Rec.AAP of a particulate water absorbing agent in accordance with an embodiment of the present invention was measured through the procedure below with use of the device (see FIG. 1) for use in the measurement under "(2) AAP" above.

First, 0.900 g of particulate water absorbing agent was spread out evenly on a plastic cylindrical cell 101 having a diameter of 60 mm and provided with a stainless-steel 400-mesh metal gauze 102 attached to the cylindrical cell 101 (see FIG. 1). A plastic piston 104 was placed on the particulate water absorbing agent, and a weight 105 was placed on the piston 104. The weight Wa (g) of the measuring device was measured.

Subsequently, the measuring device was let stand still for 1 hour in a plastic container (with a depth of 9 cm, a width of 14 cm, and a height of 5 cm) containing 400 ml of deionized water. This operation caused the particulate water absorbing agent to be immersed in deionized water for 1 hour.

Then, the cylindrical cell 101 with the weight 105 thereon was taken out from the plastic container, placed in another plastic container (with a depth of 9 cm, a width of 14 cm, and a height of 5 cm) containing 100 ml of ethanol (special grade), and was let stand still for 12 hours. This operation caused the particulate water absorbing agent to be immersed in ethanol for 12 hours.

After the above immersion in ethanol, the cylindrical cell 101 with the weight 105 thereon was taken out from the plastic container, placed on a pile of 20 pieces of filter paper (available from Advantec Toyo Kaisha, Ltd.; product name: JIS P 3801, No. 2; thickness: 0.26 mm; retaining particle diameter: 5 μm) having a diameter of 90 mm, and let stand still for 3 days.

Next, a glass filter 107 was placed in a metal vat 106, and a 0.9% aqueous sodium chloride solution 109 was poured into the metal vat 106 up to the height of the glass filter. Filter paper 108 was placed on the glass filter 107. The cylindrical cell 101, which contained the particulate water absorbing agent having been swollen with deionized water and shrunk with ethanol as described above and which had the weight 105 thereon, was placed on the filter paper 108. The particulate water absorbing agent was swollen with the 0.9% aqueous sodium chloride solution for 1 hour through a technique identical to that involved in a normal AAP measurement method. After the measurement, the weight Wb (g) of the measuring device was measured.

The Rec.AAP was calculated from the Wa and Wb, measured through the above operations, in accordance with Formula 3 below.

[Math. 3]

$$\text{Rec.AAP [g/g]} = (Wb\,[g] - Wa\,[g])/(\text{Mass of particulate water absorbing agent [g]}) \quad \text{(Formula 3)}$$

(10) Recovery SFC (Rec.SFC)

The Rec.SFC of a particulate water absorbing agent in accordance with an embodiment of the present invention was measured through the procedure below with use of the device (see FIG. 2) for use in the measurement under "(5) SFC" above.

Figure 2:
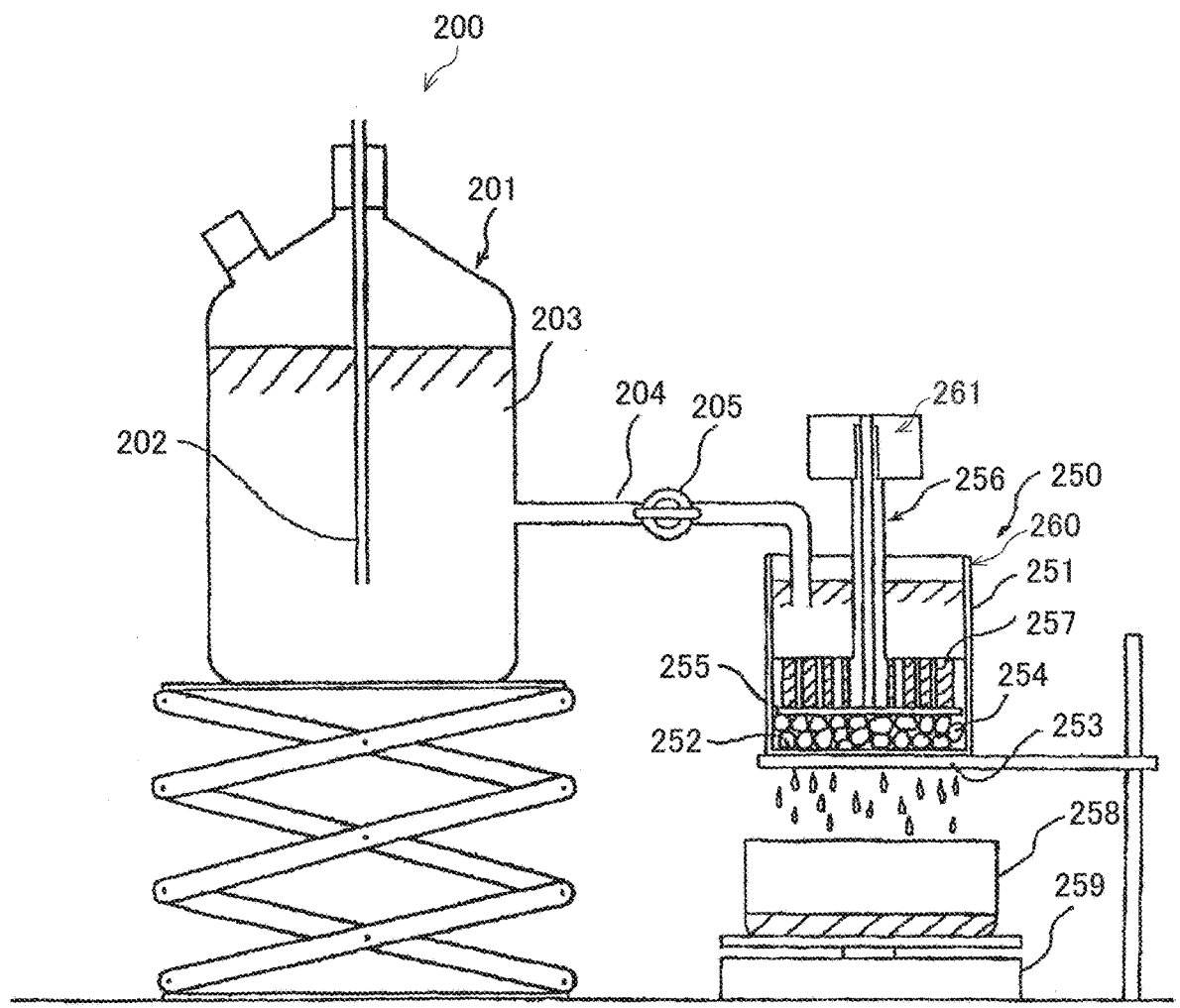
FIG. 2 is a cross-sectional view of a device for use in measuring a saline flow conductivity (SFC) and a recovery SFC (Rec.SFC).
Figure 3:
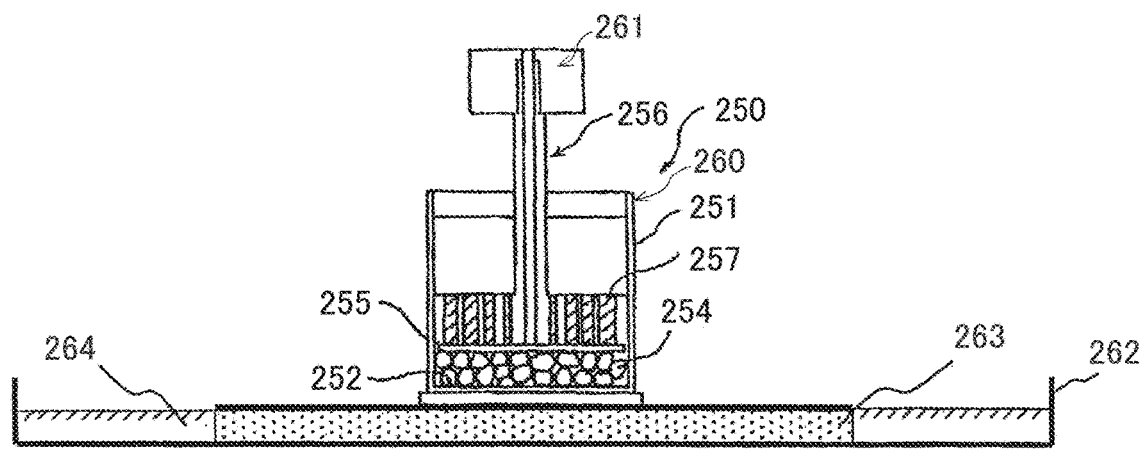
FIG. 3 is a cross-sectional view of a device for use in measuring a saline flow conductivity (SFC) and a recovery SFC (Rec.SFC).

First, 0.900 g of particulate water absorbing agent was spread out evenly on a plastic cylindrical cell 251 having a diameter of 60 mm and provided with a stainless-steel 400-mesh metal gauze 252 attached to the cylindrical cell 251 (see FIG. 2). A plastic piston 256 that had a diameter of 59 mm, that had 21 evenly spaced holes 257 each having a diameter of 9 mm, and that was provided with a stainless-steel 400-mesh metal gauze 255 attached to the bottom surface of the piston 256 was placed on the particulate water absorbing agent. Then, a lid 260 having a hole for the support column of the piston 256 to pass through and a hole for a resin tube 204 to pass through was placed on the cylindrical cell 251, and a weight 261 having a weight adjusted so as to apply a pressure of 2.07 kPa to the lower surface of the piston was placed on the piston 256. The measuring device was immersed for 1 hour in a plastic container (with a depth of 9 cm, a width of 14 cm, and a height of 5 cm) containing 400 ml of deionized water. Then, the measuring device was placed in a plastic container (with a depth of 9 cm, a width of 14 cm, and a height of 5 cm) containing 100 ml of ethanol (special grade), and was let stand still for 12 hours.

After the measuring device was let stand still in ethanol, the measuring device was taken out from the plastic container, placed on a pile of 20 pieces of filter paper (available from Advantec Toyo Kaisha, Ltd.; product name: JIS P 3801, No. 2; thickness: 0.26 mm; retaining particle diameter: 5 μm) having a diameter of 90 mm, and let stand still for 3 days. Then, a glass filter 263 was placed in a metal vat 262, and a synthesized urine 264 having the composition below was poured into the metal vat 262 up to the height of the glass filter. The cylindrical cell 251, which contained the particulate water absorbing agent having been swollen with deionized water and shrunk with ethanol as described above and which had the weight 261 thereon, was placed on the glass filter 263. The particulate water absorbing agent was swollen for 1 hour.

The synthesized urine was a mixture of 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of deionized water.

After the particulate water absorbing agent was swollen with the synthesized urine, the measuring device was placed on a support stand 253, and a resin tube 204 was inserted into the cylindrical cell 251 through the lid 260. The resin tube 204 was connected to a container 201 lidded with a rubber stopper through which a glass tube 202 having a diameter of 5 mm was inserted. The container 201 was filled with a 0.69% aqueous sodium chloride solution 203. The support stand 253 had been adjusted so that the height difference was 5 cm between the lower surface of the cylindrical cell 251 and a lower portion of the glass tube 202 and that turning on the cock 205 would let the 0.69% aqueous sodium chloride solution 203 be poured up to a height of 5 cm from the lower surface of the cylindrical cell 251. After the resin tube 204 was inserted into the cylindrical cell 251, the cock 205 was turned on so that the 0.69% aqueous sodium chloride solution was poured, and the Rec.SFC was measured similarly to normal SFC measurement.

(11) Recovery Rate (Rec.CRC/CRC)

The Rec.CRC/CRC of a particulate water absorbing agent in accordance with an embodiment of the present invention was calculated from the CRC, determined by the technique described under (1) above, and the Rec.CRC, determined by the technique described under (8) above, in accordance with Formula 4 below.

[Math. 4]

$$\text{Recovery rate} = \text{Rec.CRC/CRC} \quad \text{(Formula 4)}$$

(12) Elastic Modulus Index (EMI)

[Elastic Modulus]

(Step 1: Classifying Particulate Water Absorbing Agent)

Ten grams of particulate water absorbing agent was classified with use of six JIS standard sieves (THE IIDA TESTING SIEVE, diameter: 8 cm) having respective mesh sizes of 710 μm, 600 μm, 500 μm, 425 μm, 300 μm, and 150 μm. The classification was carried out for 5 minutes with use of a vibration classifier (IIDA SIEVE SHAKER, TYPE: ES-65, number of rotations: 60 Hz, 230 rpm; number of impacts: 60 Hz, 130 rpm, SER. No. 0501).

The step 1 above produced a particulate water absorbing agent classified on the basis of the particle size. A particulate water absorbing agent remaining on the JIS standard sieve having a mesh size of 500 μm, for example, would have particle diameters within a range of not less than 500 μm and less than 600 μm.

(Step 2: Swelling Particulate Water Absorbing Agent)

The amount of the particulate water absorbing agent classified on the basis of the particle size in the step 1 above which amount (added amount) was calculated in accordance with Formula 5 below was put into a 10-ml plastic container. Then, 8.0 g of deionized water was added to the particulate water absorbing agent, and the particulate water absorbing agent was immersed in and swollen with the deionized water for 16 hours.

[Math. 5]

$$\text{Particulate water absorbing agent [g]} = 2.0 \, g/(\text{CRCdw}+1) \quad \text{(Formula 5)}$$

Formula 5 above is a formula for calculating the amount of a particulate water absorbing agent with which amount swollen gel particles will have a weight of 2.0 g. Further, "CRCdw" in Formula 5 means the CRC (centrifuge retention capacity) that a particulate water absorbing agent has when it has been swollen with deionized water.

The CRCdw is determined as measured in "(1) CRC" above except that the 0.9 weight % aqueous sodium chloride solution has been replaced with deionized water, the amount of the sample has been changed from 0.2 g to 0.05 g, and the immersion time period has been changed from 30 minutes to 16 hours.

(Step 3: Measuring Elastic Modulus)

The elastic modulus of the particulate water absorbing agent as swollen in the step 2 above (hereinafter referred to as "swollen gel") was measured with use of a rheometer (MCR301, available from Anton-Paar) (see FIG. 4). The following description will discuss the measurement method in detail with reference to FIG. 4.

First, swollen gel 302 obtained in the step 2 above was put onto a dish 301 (inner diameter: 51 mm, depth: 10 mm, made of aluminum) of a rheometer 300 together with swelling liquid (deionized water), and was leveled off to be present evenly in the dish 301. The dish 301 was fixed to the rheometer 300. The rheometer 300 and the dish 301 were oriented strictly horizontally.

Figure 4:
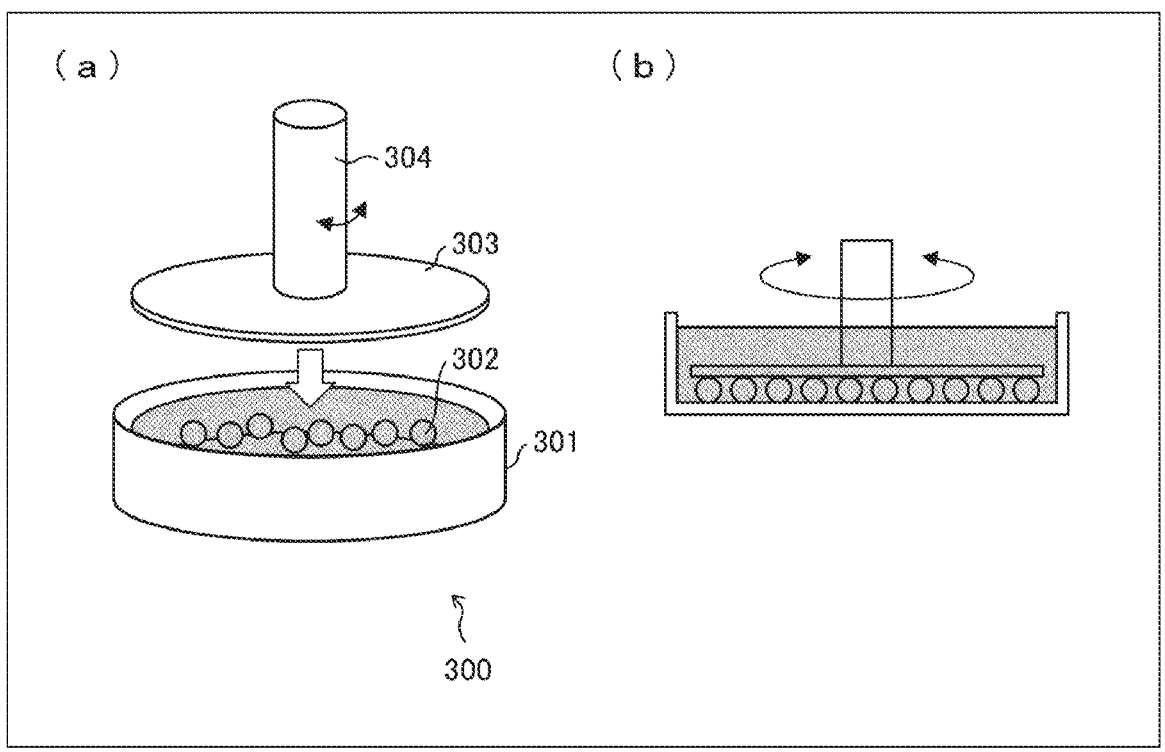
FIG. 4 shows diagrams each illustrating the appearance of a portion of a device for use in measuring the elastic modulus of a particulate water absorbing agent.

Next, a parallel plate 303 (diameter: 50 mm, made of aluminum) to which a rotary shaft 304 was attached perpendicularly thereto was fitted into the dish 301, and was then rotated in the direction indicated by the arrow in FIG. 4 to provide vibrations to the swollen gel 302. The storage elastic modulus was measured under the measurement conditions below.

<Measurement Conditions>
Measurement mode: Vibration (dynamic) measurement
Strain: 0.02%
Angular frequency: 10 rad/s
Starting time of measurement: At the time point at which the parallel plate 52 came into contact with the swollen gel 51
Vertical load: 10 N to 40 N, imposed discontinuously
Increased by 5 N each time a measurement time period of 100 seconds elapsed
Measurement intervals: 5 seconds
Number of measurement pieces: 20×7 loading conditions
Measurement time period: 700 seconds (=5 seconds×20 pieces×7 loading conditions)

The above measurement was carried out of the particulate water absorbing agent obtained in the step 1 and having different particle sizes. The dish 301 and the parallel plate 303 for use in the measurement were, for each measurement, each replaced with a new one, or washed sufficiently, dried, polished with use of a polishing cloth (available from Trusco Nakayama Corporation, base material: cotton, abrasive: abrasive A [particle size: #15000], with wax therein), and washed again before reuse.

The arithmetic average of, among storage elastic modulus values obtained during the above measurement, a total of 20 measurement values obtained during a measurement time period of 600 seconds to 700 seconds (with a load of 40 N) was used as an elastic modulus G' (unit: Pa) of an embodiment of the present invention.

[Calculating Elastic Modulus Index (EMI)]

The elastic modulus index (EMI) was calculated from the respective values of CRC, CRCdw, and elastic modulus in accordance with Formulae (6) to (14) below. The elastic modulus index is a value obtained by correcting an elastic modulus G' on the basis of a theoretical surface area and CRC of swollen gel, and is a value that serves as an index for evaluation of the performance of a particulate water absorbing agent. The description below uses the acronym "EMI" to refer to "elastic modulus index".

[Math. 6]

$$\text{EMI} = \text{Elastic modulus } G'/(\text{theoretical surface area (TGS) of swollen gel particles}) \times \text{CRC} \quad \text{(Formula 6)}$$

In Formula (6) above, "CRC" refers to a CRC value measured of a particulate water absorbing agent before the step 1 is carried out for measurement of the elastic modulus, and is measured by the method described in (1). Further, "swelling gel" is that which is obtained in the step 2 for measurement of the elastic modulus.

The numerical values (A) to (I) necessary for the calculation of the EMI are calculated in accordance with Formulae (7) to (14) below.

[Math. 7]

$$\text{TGS [cm}^2\text{]} = \text{Theoretical surface area } (A) \text{ of single swollen gel particle [cm}^2\text{]} \times \text{number } (B) \text{ of particles in measurement} \quad \text{(Formula 7)}$$

[Math. 8]

$$\text{Theoretical surface area } (A) \text{ of single swollen gel particle [cm}^2\text{]} = 4 \times \pi \times (\text{theoretical radius } (C) \text{ of single swollen gel particle})^2 \quad \text{(Formula 8)}$$

[Math. 9]

$$\text{Theoretical radius } (C) \text{ of single swollen gel particle [cm]} = (\text{Volume } (D) \text{ of single swollen gel particle} \times 3/4 \times 1/\pi)^{1/3} \quad \text{(Formula 9)}$$

[Math. 10]

$$\text{Volume } (D) \text{ of single swollen gel particle [cm}^3\text{]} = 2.0/\text{number } (B) \text{ of particles before swelling} \quad \text{(Formula 10)}$$

[Math. 11]

$$\text{Number } (B) \text{ of particles before swelling} = \text{Weight } (E) \text{ of particulate water absorbing agent}/(\text{theoretical volume } (F) \text{ of single particle before swelling} \times 1.6) \quad \text{(Formula 11)}$$

[Math. 12]

$$\text{Theoretical volume } (F) \text{ of single particle before swelling [cm}^3\text{]} = 4/3 \times \pi \times (\text{diameter } (G) \text{ of intermediate particles before swelling}/2)^3 \quad \text{(Formula 12)}$$

[Math. 13]

$$\text{Diameter } (G) \text{ of intermediate particles before swelling [cm]} = (\text{Mesh size } (H) \text{ of upper sieve for classification} + \text{mesh size } (I) \text{ of lower sieve for classification})/2 \quad \text{(Formula 13)}$$

[Math. 14]

$$\text{Weight } (E) \text{ of particulate water absorbing agent [g]} = 2.0/(\text{CRCdw} + 1) \quad \text{(Formula 14)}$$

(13) Diffusion Absorbency Period

Figure 5:
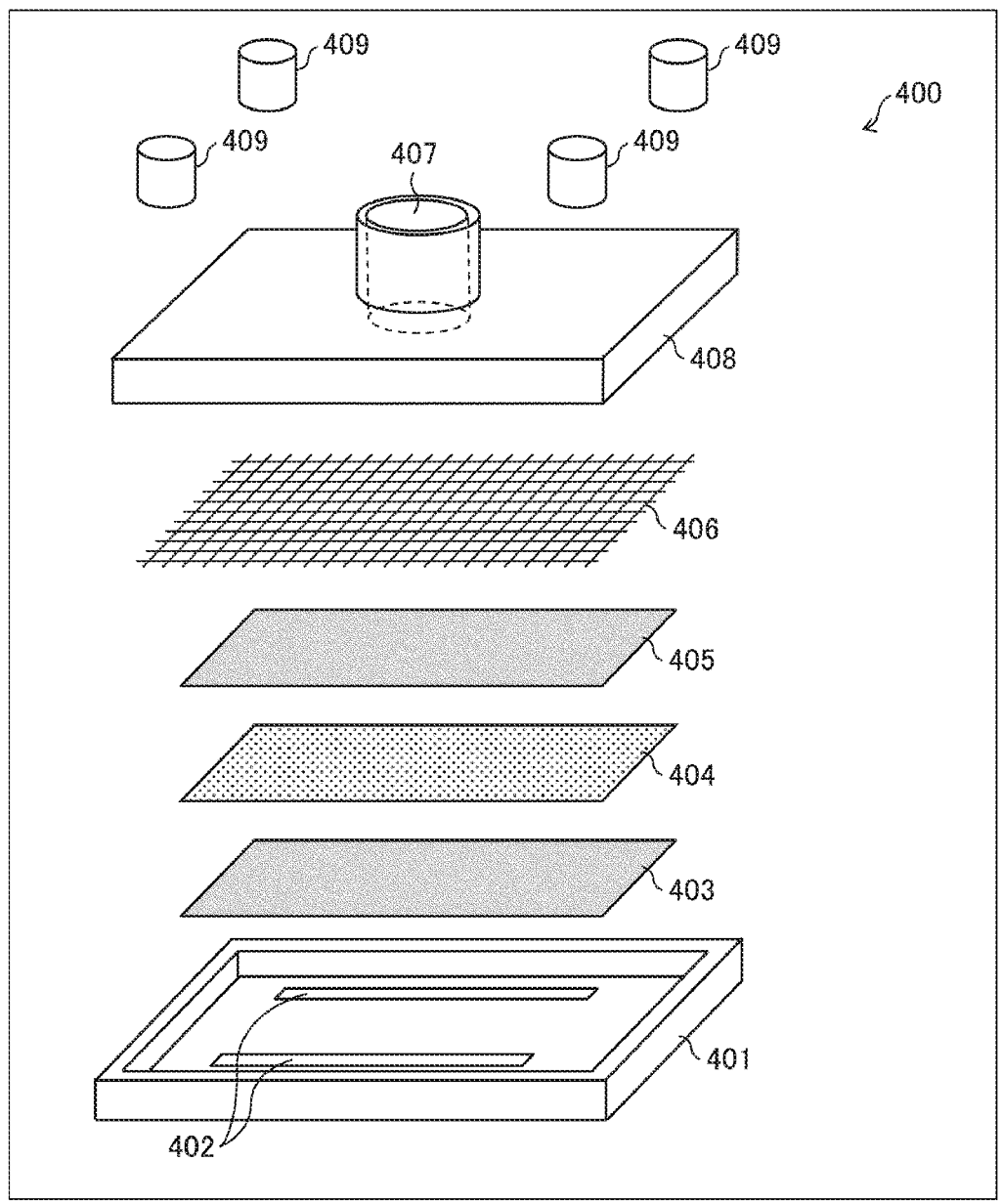
FIG. 5 is a diagram schematically illustrating the structure of a measuring device for use in measuring a diffusion absorbency period.

The diffusion absorbency period [sec] of a particulate water absorbing agent in accordance with an embodiment of the present invention was measured with use of a diffusion absorbency period measuring device (see FIGS. 5 and 6) by the method described below. The measurement involved use of a diffusion absorbency period measuring device of which the appearance is schematically illustrated in FIG. 5.

First, to a central portion of an acrylic resin tray 401 having internal dimensions of 401 mm (width)×151 mm (length)×30 mm (height) and external dimensions of 411 mm (width)×161 mm (length)×35 mm (height), two strips of double-side tape (available from Nichiban Co., Ltd.; double-side tape NICETACK NW-10) 402 each having a width of 10 mm and a length of 300 mm were attached in such a pattern as to extend along respective corresponding widthwise inner walls and to be separated from respective widthwise ends by 50 mm. To the double-side tape 402, a tissue 403 that had a thickness of 0.1 mm, a width of 300 mm, and a length of 150 mm (prepared by cutting Kimwipe L-100 available from Nippon Paper Crecia Co., Ltd. into the above dimensions) was attached in such a manner that the water-absorbing sheet 403 was not wrinkled.

Next, 2.7 g of wood-ground pulp was moistened by spraying mist onto the pulp for 5 seconds with use of an ultrasonic moistening device (available from Nippo Co., Ltd.; NP-408; atomizing capability: 600 g/hr). The moistened pulp and 13.5 g±0.010 g of particulate water absorbing agent were put into a food processor (available from Panasonic Corporation; MK-K48P), and were crushed and mixed for 5 seconds to prepare an absorbent body. In a case where the pulp and the particulate water absorbing agent were not mixed uniformly, the mixing time period was extended.

The absorbent body prepared through the above operation was spread out evenly on a tissue 403 on an acrylic resin tray 401 over an area that had a width of 300 mm and a length of 120 mm and that was 15 mm inward of each widthwise inner wall of the acrylic resin tray 401. Before the spraying, a static electricity preventing treatment was carried out on the wall surface of the acrylic resin tray 401 for prevention of static electricity.

A top sheet 405 was placed on the sprayed absorbent body 404. The top sheet 405 was positioned so as to be separated from each lengthwise inner wall of the acrylic resin tray 401 by an equivalent distance and from each widthwise inner wall thereof by an equivalent distance.

The top sheet 405 was a sheet taken out from a Mamy Poko (product name) tape type (size L, purchased in Japan in June 2014; number on the package bottom surface: 404088043) available from Unicharm Corporation. The sheet taken out had a length of 14 cm, a width of 39 cm, and a weight of 3.3 g to 3.6 g. Pulp and the like in the disposable diaper that had adhered to the sheet with an adhesive were sufficiently removed before the use.

A metal gauze 406 (JIS metal gauze; made of stainless steel; 20-mesh) having a width of 390 mm, a length of 90 mm, and a thickness of 0.63 mm was placed on the top sheet 405. Further, an acrylic resin lid 408 (with a width of 400 mm, a length of 150 mm, and a thickness of 20 mm) having, at a central portion thereof, a cylindrical inlet 407 (with a cylindrical portion having a height of 100 mm) having a diameter of 30 mm was placed on the metal gauze 406.

Figure 6:
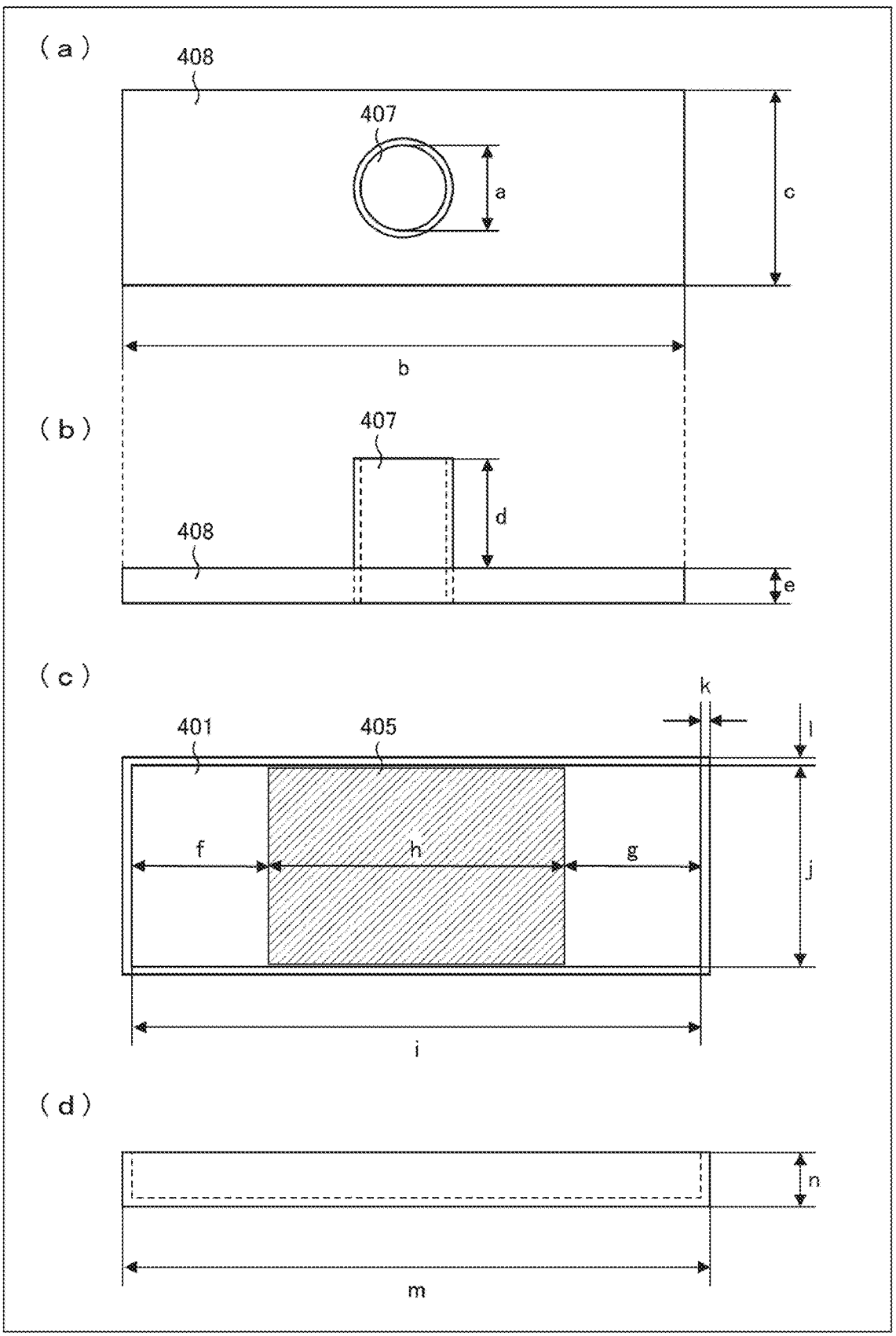
FIG. 6 shows diagrams illustrating the respective appearances of a lid and tray of a measuring device for use in measuring a diffusion absorbency period. (a) of FIG. 6 is a top view of the lid. (b) of FIG. 6 is a side view of the lid. (c) of FIG. 6 is a top view of the tray. (d) of FIG. 6 is a side view of the tray.

FIG. 6 shows diagrams illustrating respective appearances of a lid and a tray of a measuring device used for measuring a diffusion absorbency period. (a) of FIG. 6 is a top view of the lid. (b) of FIG. 6 is a side view of the lid. (c) of FIG. 6 is a top view of the tray. (d) of FIG. 6 is a side view of the tray.

(a) of FIG. 6 shows the symbol "a" to indicate the diameter of the inlet 407, the symbol "b" to indicate the width of the lid 408, and the symbol "c" to indicate the length of the lid 408. (b) of FIG. 6 shows the symbol "d" to indicate the height of the cylindrical portion of the inlet 407 and the symbol "e" to indicate the thickness of the lid 408.

(c) of FIG. 6 shows how the tissue 403 is positioned on the acrylic resin tray 401. (c) of FIG. 6 shows the symbols "f" and "g" to indicate that the tissue 403 is 50.5 mm apart inward from the lengthwise inner walls, the symbol "h" to indicate the width (300 mm) of the tissue 403, the symbol "i" to indicate the widthwise internal dimension (401 mm) of the acrylic resin tray 401, the symbol "j" to indicate the internal length (151 mm) of the acrylic resin tray 401 and the length (151 mm) of the tissue 403, the symbol "k" to indicate the widthwise difference (5 mm) between the internal dimension and external dimension of the acrylic resin tray 401, and the symbol "l" to indicate the lengthwise difference (5 mm) between the internal dimension and external dimension of the acrylic resin tray 401.

(d) of FIG. 6 shows the symbol "m" to indicate the external width (411 mm) of the acrylic resin tray 401 and the symbol "n" to indicate the height (35 mm) of the acrylic resin tray 401.

Weights 409 were placed on the lid 408 for an even load on the absorbent body 404. The respective weights and the like of the weights 409 were adjusted so that the total weight of the metal gauze 406, the acrylic resin lid 408, and the weights 409 was 7485 g or 22770 g (the load applied a pressure of 2.07 kPa or 6.21 kPa to the area in which the absorbent body was dispersed).

Then, 75 g of a 0.9 weight % aqueous sodium chloride solution (preferably colored with 0.04 g of blue No. 1 with respect to 1000 g of the aqueous solution) having a temperature adjusted to 37° C.±0.5° C. was introduced over a period of 5 seconds through the inlet 407 into the diffusion absorbency period measuring device 400. The aqueous sodium chloride solution introduced was diffused on the metal gauze 406 while passing through the metal gauze 406, and was thereafter absorbed by the absorbent body 404. The liquid retained in the mesh openings of the metal gauze 406 was all absorbed. The time period spent for the absorption was referred to as a first-time diffusion absorbency period [sec].

Subsequently, 10 minutes after the start of the first-time introduction of the above aqueous solution, the aqueous solution was introduced for the second time. The aqueous solution retained in the mesh openings of the metal gauze 406 was all absorbed. The time period spent for the absorption was referred to as a second-time diffusion absorbency period [sec]. Similarly, 10 minutes after the start of introducing the aqueous solution the second time, the aqueous solution retained in the mesh openings of the metal gauze 406 was all absorbed. The time period spent for the absorption was referred to as a third-time diffusion absorbency period [sec].

Example 1

First, in a polypropylene container having an inner diameter of 50 mm and a capacity of 120 mL, 23.2 g of acrylic acid, 0.135 g (0.080 mol %) of polyethyleneglycol diacrylate (with a weight average molecular weight [Mw] of 523), 0.071 g of a 2.0 weight % aqueous diethylenetriamine pentaacetic acid/trisodium solution, 22.2 g of ion-exchange water, and 9.6 g of a 48.5 weight % aqueous sodium hydroxide solution were mixed with each other to prepare a solution (A).

While the solution (A) having a temperature adjusted to 45° C. was being stirred with use of a magnetic stirrer, 9.8 g of a 48.5 weight % aqueous sodium hydroxide solution was added over approximately 5 seconds and mixed in an open system to prepare an aqueous monomer solution (1). Heat of neutralization and heat of dissolution caused during the mixing increased the temperature of the aqueous monomer solution (1) to approximately 80° C.

Subsequently, when the temperature of the aqueous monomer solution (1) reached 78° C., 1.01 g of a 4.5 weight % aqueous sodium persulfate solution was added, and the resulting mixture was stirred for approximately 3 seconds. Then, the resulting reaction liquid (1) was poured into a stainless-steel petri dish in an open system.

The stainless-steel petri dish had an inner diameter of 88 mm and a height of 20 mm. The stainless-steel petri dish had a surface temperature heated in advance to 50° C. with use of a hot plate (NEO HOTPLATE H1-1000; available from Iuchi Seiei Do Ltd.).

Immediately after the reaction liquid (1) was supplied, the stainless-steel petri dish was covered by a glass container having a discharge opening, and the inside air was sucked with use of a vacuum pump so that the pressure inside the casing was 85 kPa as a gage pressure. The pressure outside the casing was 101.3 kPa (atmospheric pressure).

A while after the reaction liquid (1) was poured into the stainless-steel petri dish, polymerization started. The polymerization proceeded upward with water vapor being generated and the mixture expanding and foaming in various directions. The mixture was then contracted to a size slightly larger than the bottom surface of the petri dish. The expansion and contraction ended within approximately 1 minute.

Then, the mixture was retained in the polymerization container (that is, the stainless-steel petri dish covered by the glass container) for 3 minutes, and a crosslinked hydrogel polymer (hereinafter referred to as "hydrogel") (1) was then taken out.

The hydrogel (1) obtained was gel-crushed with use of a screw extruder (meat chopper) having the specifications below. The screw extruder included a porous plate at a tip thereof, the porous plate having a diameter of 82 mm, a pore diameter of 8.0 mm, 33 pores, and a thickness of 9.5 mm. Regarding conditions for the gel-crushing, the hydrogel (1) was put in an amount of approximately 360 g/min while 90° C. deionized water was being added at 50 g/min for gel-crushing.

The gel-crushed hydrogel (1) was spread out on a stainless-steel metal gauze having a mesh size of 850 µm and dried with 190° C. hot air for 30 minutes. Subsequently, the dry polymer (1) prepared through the drying operation was crushed with use of a roll mill (available from Inoguchi Giken Ltd.; WML-type roll crusher), and was then classified with use of JIS standard sieves having respective mesh sizes of 710 µm and 175 µm.

The above operations produced water-absorbing resin powder (1) ground to have uneven shapes and having a solid content of 96.4% by weight, a weight average particle diameter (D50) of 395 µm, and a logarithmic standard deviation (σζ) of a particle size distribution of 0.35. The water-absorbing resin powder (1) had a centrifuge retention capacity (CRC) of 38.6 g/g and a water-soluble content (Ext) of 10.8% by weight, and contained particles with a particle diameter of less than 150 µm at a proportion of 1.2% by weight.

With 100 parts by weight of the water-absorbing resin powder (1), a surface-crosslinking agent solution (1) containing 0.4 parts by weight of ethylene carbonate, 0.6 parts by weight of propylene glycol, 6.0 parts by weight of deionized water, and 0.001 parts by weight (10 ppm with respect to the water-absorbing resin powder) of polyoxyethylene (20) sorbitane monostearate (available from Kao Corporation) were mixed uniformly.

Then, the moistened mixture (1) obtained was put into an airtight container, and the temperature was maintained at 80° C. for 6 hours. Then, the mixture was heat-treated at 212° C. for approximately 35 minutes so that the resulting water-absorbing resin particles would have a CRC within a range of 26.7 g/g to 27.7 g/g.

After the heat treatment, the resulting water-absorbing resin particles were crushed until they passed through a JIS standard sieve having a mesh size of 850 µm. This prepared surface-crosslinked water-absorbing resin particles (1).

To 100 parts by weight of the surface-crosslinked water-absorbing resin particles (1), 1.325 parts by weight of a mixed liquid containing 1 part by weight of a 27 weight % aqueous aluminum sulfate solution (8% by weight based on aluminum oxide), 0.3 parts by weight of a 60 weight % aqueous sodium lactate solution, and 0.025 parts by weight of 1,2-propylene glycol were added.

After the above addition, the mixture was dried windlessly at 60° C. for 30 minutes. Then, the dried product was crushed until it passed through a JIS standard sieve having a mesh size of 850 µm. Then, 30 g of the crushed particles were put into a glass container having a diameter of 6 cm and a height of 11 cm. Then, 10 g of glass beads each having a diameter of 6 mm were added. The glass container was attached to a paint shaker (available from Toyo Seiki Seisaku-sho, Ltd.; No. 488; the details of the device are disclosed in Japanese Patent Application Publication, Tokukaihei, No. 9-235378), and was shaken at 800 cycles per min (CPM) for 10 minutes.

After the 10-minute shaking, the glass beads were removed with use of a JIS standard sieve having a mesh size of 2 mm. This produced a particulate water absorbing agent (1).

The Rec.CRC/CRC, Rec.AAP, Rec.SFC, and EMI of the particulate water absorbing agent (1) produced as above were measured and calculated. Table 1 shows the results. Table 2 shows the results of measuring the elastic modulus for each particle size range.

Example 2

Operations similar to those of Example 1 were carried out except that the amount of polyethyleneglycol diacrylate (with a weight average molecular weight [Mw] of 523) was changed from 0.135 g (0.080 mol %) to 0.101 g (0.060 mol %) and that the heat treatment was carried out so that the resulting water-absorbing resin particles would have a CRC within a range of 29.5 g/g to 30.5 g/g. This produced a particulate water absorbing agent (2).

The Rec.CRC/CRC, Rec.AAP, Rec.SFC, and EMI of the particulate water absorbing agent (2) produced as above were measured and calculated. Table 1 shows the results. Table 3 shows the results of measuring the elastic modulus for each particle size range.

Comparative Example 1

Operations similar to those of Example 1 were carried out except that the pressure inside the casing was changed to atmospheric pressure (101.3 kPa). This produced a comparative particulate water absorbing agent (1).

The Rec.CRC/CRC, Rec.AAP, Rec.SFC, and EMI of the comparative particulate water absorbing agent (1) produced as above were measured and calculated. Table 1 shows the results. Table 4 shows the results of measuring the elastic modulus for each particle size range.

Comparative Example 2

Operations similar to those of Example 1 were carried out except that the amount of polyethyleneglycol diacrylate (with a weight average molecular weight [Mw] of 523) was changed from 0.135 g (0.080 mol %) to 0.338 g (0.200 mol %) and that the surface treatment step was not carried out. This produced a comparative particulate water absorbing agent (2).

The Rec.CRC/CRC, Rec.AAP, Rec.SFC, and EMI of the comparative particulate water absorbing agent (2) produced as above were measured and calculated. Table 1 shows the results. Table 5 shows the results of measuring the elastic modulus for each particle size range.

Comparative Example 3

Water-absorbing resin was taken out from a disposable diaper (available from Procter & Gamble; product name:

Pampers Sarasara Care Pants) purchased in Japan in May 2013, and was used as a comparative particulate water absorbing agent (3).

The Rec.CRC/CRC, Rec.AAP, Rec.SFC, and EMI of the comparative particulate water absorbing agent (3) produced as above were measured and calculated. Table 1 shows the results. Table 6 shows the results of measuring the elastic modulus for each particle size range.

Comparative Example 4

Water-absorbing resin was taken out from a disposable diaper (available from Ontex; product name: Canbebe) purchased in Pakistan in December 2014, and was used as a comparative particulate water absorbing agent (4).

The Rec.CRC/CRC, Rec.AAP, Rec.SFC, and EMI of the comparative particulate water absorbing agent (4) produced as above were measured and calculated. Table 1 shows the results. Table 7 shows the results of measuring the elastic modulus for each particle size range.

Comparative Example 5

Water-absorbing resin was taken out from a disposable diaper (available from Procter & Gamble; product name: Pampers Easy Up Pants; size: 4 Maxi) purchased in Belgium in June 2013, and was used as a comparative particulate water absorbing agent (5).

The Rec.CRC/CRC, Rec.AAP, Rec.SFC, and EMI of the comparative particulate water absorbing agent (5) produced as above were measured and calculated. Table 1 shows the results. Table 8 shows the results of measuring the elastic modulus for each particle size range.

Comparative Example 6

Water-absorbing resin was taken out from a disposable diaper (available from Procter & Gamble; product name: Pampers Cruisers; size: 4 Maxi) purchased in Poland in February 2013, and was used as a comparative particulate water absorbing agent (6).

The Rec.CRC/CRC, Rec.AAP, Rec.SFC, and EMI of the comparative particulate water absorbing agent (6) produced as above were measured and calculated. Table 1 shows the results. Table 9 shows the results of measuring the elastic modulus for each particle size range.

Comparative Example 7

Water-absorbing resin was taken out from a disposable diaper (available from Unicharm Corporation; product name: Mamy Poko Pants; size: L) purchased in Indonesia in October 2011, and was used as a comparative particulate water absorbing agent (7).

The Rec.CRC/CRC, Rec.AAP, Rec.SFC, and EMI of the comparative particulate water absorbing agent (7) produced as above were measured and calculated. Table 1 shows the results. Table 10 shows the results of measuring the elastic modulus for each particle size range.

Comparative Example 8

Water-absorbing resin was taken out from a disposable diaper (available from Kimberly-Clark Corp.; product name: HUGGIES; size: 4 Maxi) purchased in Turkey in April 2013, and was used as a comparative particulate water absorbing agent (8).

The Rec.CRC/CRC, Rec.AAP, Rec.SFC, and EMI of the comparative particulate water absorbing agent (8) produced as above were measured and calculated. Table 1 shows the results. Table 11 shows the results of measuring the elastic modulus for each particle size range.

Comparative Example 9

Operations similar to those of Example 1 were carried out except that the temperature of the moistened mixture (1) obtained was not maintained at 80° C. for 6 hours, but the mixture was immediately heat-treated at 212° C. for approximately 35 minutes so that the resulting water-absorbing resin particles would have a CRC within a range of 26.7 g/g to 27.7 g/g. This produced a comparative particulate water absorbing agent (9). The Rec.CRC/CRC, Rec.AAP, Rec.SFC, and EMI of the comparative particulate water absorbing agent (9) produced as above were measured and calculated. Table 1 shows the results. Table 12 shows the results of measuring the elastic modulus for each particle size range.

Example 3

The diffusion absorbency periods of the particulate water absorbing agent (1) produced in Example 1 were measured. Table 13 shows the measurement results.

Comparative Example 10

The diffusion absorbency periods of the comparative particulate water absorbing agent (1) produced in Comparative Example 1 were measured. Table 13 shows the measurement results.

Comparative Example 11

The diffusion absorbency periods of the comparative particulate water absorbing agent (9) produced in Comparative Example 9 were measured. Table 13 shows the measurement results.

TABLE 1

|  | EMI (600-500 μm) | Rec. CRC/ CRC | Rec. AAP | Rec. SFC |
|---|---|---|---|---|
| Example 1 | 6831 | 1.08 | 18 | 12 |
| Example 2 | 6205 | 1.11 | 20 | 10 |
| Comparative Example 1 | 5399 | 1.13 | 11 | 4 |
| Comparative Example 2 | 8282 | 1.02 | 9 | 1 |
| Comparative Example 3 | 4882 | 1.11 | 8 | 3 |
| Comparative Example 4 | 5044 | 1.07 | 11 | 0 |
| Comparative Example 5 | 6037 | 1.01 | 9 | 5 |
| Comparative Example 6 | 8033 | 1.00 | 8 | 7 |
| Comparative Example 7 | 4681 | 1.15 | 7 | 0 |
| Comparative Example 8 | 3878 | 1.25 | 4 | 0 |
| Comparative Example 9 | 6152 | 1.04 | 13 | 7 |

TABLE 2

| | | Mesh size of upper sieve for classification [μm] | Mesh size of lower sieve for classification [μm] | CRCdw [g/g] | Elastic modulus G' [Pa] | EMI |
|---|---|---|---|---|---|---|
| Example 1 | Particulate water absorbing agent (1) | 710 | 600 | 169 | 7889 | 7581 |
| | | 600 | 500 | 166 | 8524 | 6831 |
| | | 500 | 425 | 161 | 9482 | 6319 |
| | | 425 | 300 | 150 | 11056 | 5646 |
| | | 300 | 150 | 129 | 14052 | 4236 |

TABLE 3

| | | Mesh size of upper sieve for classification [μm] | Mesh size of lower sieve for classification [μm] | CRCdw [g/g] | Elastic modulus G' [Pa] | EMI |
|---|---|---|---|---|---|---|
| Example 2 | Particulate water absorbing agent (2) | 710 | 600 | 229 | 5699 | 6683 |
| | | 600 | 500 | 226 | 6334 | 6205 |
| | | 500 | 425 | 221 | 7292 | 5958 |
| | | 425 | 300 | 210 | 8866 | 5586 |
| | | 300 | 150 | 189 | 11862 | 4479 |

TABLE 4

| | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 1 | Comparative particulate water absorbing agent (1) | 710 | 600 | 177 | 5973 | 5850 |
| | | 600 | 500 | 174 | 6608 | 5399 |
| | | 500 | 425 | 169 | 7566 | 5143 |
| | | 425 | 300 | 158 | 9140 | 4766 |
| | | 300 | 150 | 137 | 12136 | 3746 |

TABLE 5

| | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 2 | Comparative particulate water absorbing agent (2) | 710 | 600 | 145 | 10094 | 9354 |
| | | 600 | 500 | 142 | 10729 | 8282 |
| | | 500 | 425 | 137 | 11687 | 7487 |
| | | 425 | 300 | 126 | 13261 | 6483 |
| | | 300 | 150 | 105 | 16257 | 4643 |

TABLE 6

| | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 3 | Comparative particulate water | 710 | 600 | 245 | 4094 | 5057 |
| | | 600 | 500 | 242 | 4729 | 4882 |
| | | 500 | 425 | 237 | 5687 | 4899 |

TABLE 6-continued

|  | | Mesh size of upper sieve for classification [μm] | Mesh size of lower sieve for classification [μm] | CRCdw [g/g] | Elastic modulus G' [Pa] | EMI |
|---|---|---|---|---|---|---|
|  | absorbing agent (3) | 425 | 300 | 226 | 7261 | 4829 |
|  |  | 300 | 150 | 205 | 10257 | 4099 |

TABLE 7

|  | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 4 | Comparative particulate water absorbing agent (4) | 710 | 600 | 249 | 3821 | 5175 |
|  |  | 600 | 500 | 246 | 4456 | 5044 |
|  |  | 500 | 425 | 241 | 5414 | 5115 |
|  |  | 425 | 300 | 230 | 6988 | 5098 |
|  |  | 300 | 150 | 209 | 9984 | 4379 |

TABLE 8

|  | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 5 | Comparative particulate water absorbing agent (5) | 710 | 600 | 186 | 6705 | 6934 |
|  |  | 600 | 500 | 176 | 7071 | 6037 |
|  |  | 500 | 425 | 167 | 8011 | 5643 |
|  |  | 425 | 300 | 157 | 8950 | 4843 |
|  |  | 300 | 150 | 130 | 12663 | 3999 |

TABLE 9

|  | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 6 | Comparative particulate water absorbing agent (6) | 710 | 600 | 137 | 10671 | 9106 |
|  |  | 600 | 500 | 134 | 11306 | 8033 |
|  |  | 500 | 425 | 129 | 12264 | 7226 |
|  |  | 425 | 300 | 118 | 13838 | 6211 |
|  |  | 300 | 150 | 97 | 16834 | 4394 |

TABLE 10

|  | | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 7 | Comparative particulate water | 710 | 600 | 330 | 3645 | 5277 |
|  |  | 600 | 500 | 326 | 3867 | 4681 |
|  |  | 500 | 425 | 319 | 3865 | 3906 |

TABLE 10-continued

|  | Mesh size of upper sieve for classification [μm] | Mesh size of lower sieve for classification [μm] | CRCdw [g/g] | Elastic modulus G' [Pa] | EMI |
|---|---|---|---|---|---|
| absorbing agent (7) | 425 | 300 | 312 | 3864 | 3038 |
|  | 300 | 150 | 301 | 4125 | 1988 |

TABLE 11

|  |  | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 8 | Comparative particulate water absorbing agent (8) | 710 | 600 | 324 | 3616 | 4822 |
|  |  | 600 | 500 | 343 | 3401 | 3878 |
|  |  | 500 | 425 | 344 | 3546 | 3405 |
|  |  | 425 | 300 | 346 | 3691 | 2782 |
|  |  | 300 | 150 | 316 | 4507 | 2046 |

TABLE 12

|  |  | Mesh size of upper sieve for classification [μm] | Mesh size of lower sieve for classification [μm] | CRCdw [g/g] | Elastic modulus G' [Pa] | EMI |
|---|---|---|---|---|---|---|
| Comparative Example 9 | Comparative particulate water absorbing agent (9) | 710 | 600 | 175 | 6838 | 6721 |
|  |  | 600 | 500 | 172 | 7473 | 6152 |
|  |  | 500 | 425 | 167 | 8431 | 5750 |
|  |  | 425 | 300 | 156 | 10005 | 5233 |
|  |  | 300 | 150 | 135 | 13001 | 4023 |

TABLE 13

|  |  | | Diffusion absorbency period (sec) | |
|---|---|---|---|---|
| Particulate water absorbing agent | Load (kPa) | First time | Second time | Third time |
| Example 3 Particulate water absorbing agent (1) | 2.07 | 24 | 33 | 62 |
|  | 6.21 | 34 | 67 | 125 |
| Comparative Example 10 Comparative particulate water absorbing agent (1) | 2.07 | 30 | 41 | 72 |
|  | 6.21 | 47 | 90 | 206 |
| Comparative Example 11 Comparative particulate water absorbing agent (9) | 2.07 | 27 | 38 | 69 |
|  | 6.21 | 40 | 79 | 170 |

(Recap)

Figure 7:
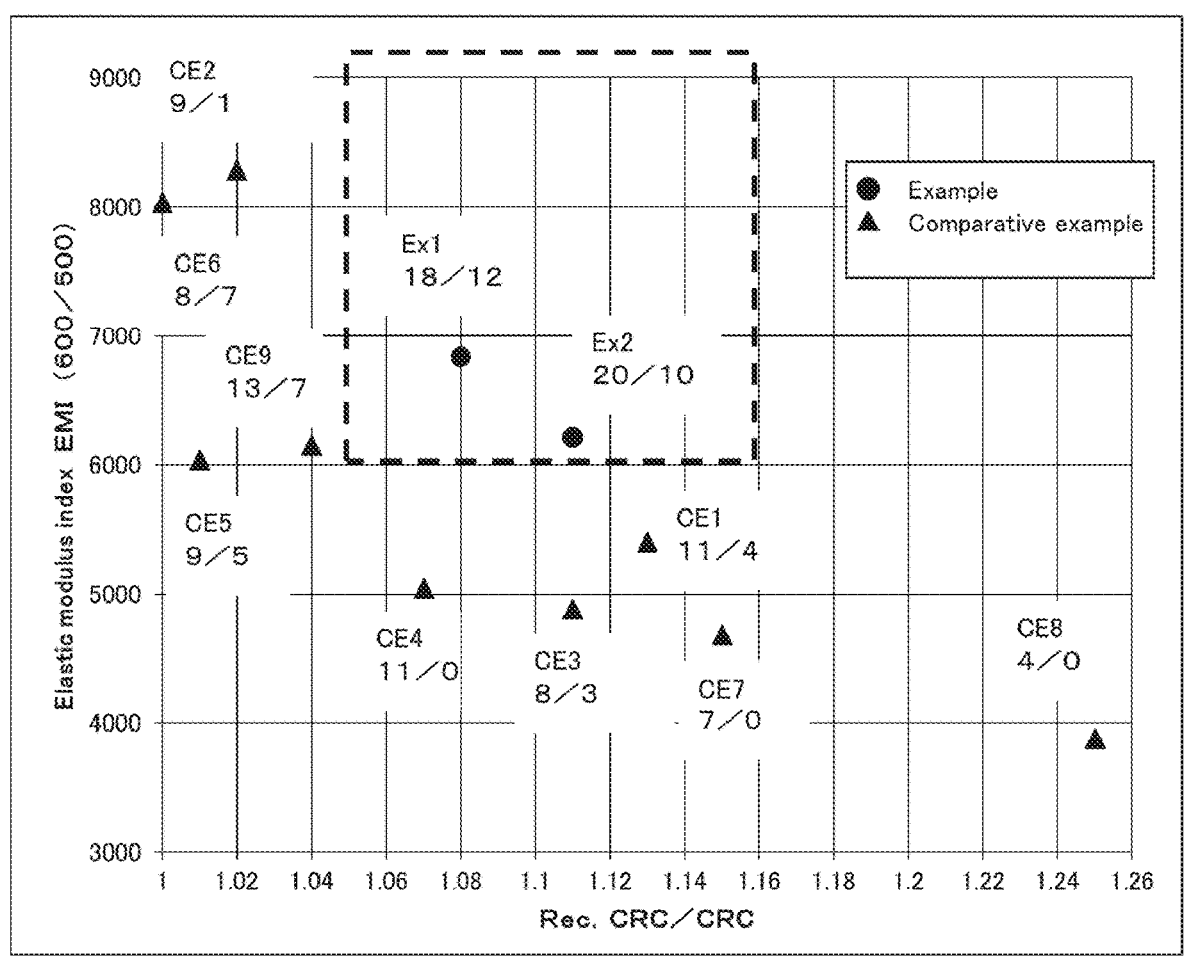
FIG. 7 is a graph that shows how the recovery rate (Rec.CRC/CRC) and the elastic modulus index (EMI) are correlated to each other.

FIG. 7 is a graph that plots, on a horizontal axis, "Rec. CRC/CRC" of each particulate water absorbing agent produced in an Example or Comparative Example and, on a vertical axis, "EMI (600/500)" of each particulate water absorbing agent produced in an Example or Comparative Example. The plotted symbols are labeled as "Ex" for "Example" or "CE" for "Comparative Example" with "Value of 'Rec.AAP'/Value of 'Rec.SFC'". The "EMI (600/500)" means the elastic modulus index of particles with a particle diameter of not less than 500 μm and less than 600 μm.

FIG. 7 shows that each particulate water absorbing agent in accordance with an embodiment of the present invention ("Ex1" and "Ex2"), which had a recovery rate (Rec.CRC/CRC) within a range of 1.05 to 1.20 and which had an elastic modulus index (EMI) (600/500) of not less than 5500, had an excellent Rec.AAP value of not less than 15 g/g and an excellent Rec.SFC value of not less than $5 \times 10^{-7} \cdot cm3 \cdot s \cdot g^{-1}$.

FIG. 7 also shows that some comparative particulate water absorbing agents had a high recovery rate but a low elastic modulus index ("CE1", "CE3", "CE4", "CE7", and "CE8") while the others had a high elastic modulus index but a low recovery rate ("CE2", "CE5", "CE6", and "CE9") and that each comparative particulate water absorbing agent had a low Rec.AAP and a low Rec.SFC. This is presumably for the reason below.

Rec.AAP and Rec.SFC refer to the fluid retention capacity under pressure and liquid permeability of a particulate water absorbing agent that has been swollen once with deionized water and that thus has a surface-crosslinked layer damaged through swelling at a rate extremely higher than in actual use. A particulate water absorbing agent having a high Rec.AAP and a high Rec.SFC is thus presumed to have a water absorption performance that becomes degraded less in a case where the particulate water absorbing agent absorbs urine or the like a plurality of times or even in a case where a disposable diaper containing the particulate water absorbing agent is used once and is then washed with water.

A particulate water absorbing agent in accordance with an embodiment of the present invention has an excellent elastic modulus index and will have a high water absorption performance even under a high pressure. Example 3 and Comparative Examples 10 and 11 indicate that a particulate absorbing agent in accordance with an embodiment of the present invention has an excellent diffusion absorbency speed even under a heavy load of not less than 22 kg.

The experimental results allow for the understanding that a particulate water absorbing agent produced by a technique in accordance with an embodiment of the present invention, which had a recovery rate (Rec.CRC/CRC) of 1.05 to 1.20 and which contained particles with a particle diameter of not less than 500 μm and less than 600 μm that had an elastic modulus index (EMI) of not less than 5500, had physical properties that were only minimally degraded after the particulate water absorbing agent had been swollen with deionized water, and exhibited an excellent Rec.AAP value of not less than 15 g/g and an excellent Rec.SFC value of not less than $5 \times 10^{-7} \cdot cm^3 \cdot s \cdot g^{-1}$.

Example 3 and Comparative Examples 10 and 11 indicate that in a case where the particulate water absorbing agent of Example 3, which satisfied all the above conditions, is used for an absorbent body, the absorbent body has a water absorption performance that becomes degraded less even under a heavy load.

Therefore, in a case where a particulate water absorbing agent in accordance with an embodiment of the present invention is used for an absorbent body, the absorbent body has an excellent liquid absorption property under a high pressure and has a high performance.

INDUSTRIAL APPLICABILITY

A particulate water absorbing agent in accordance with an embodiment of the present invention and a particulate water absorbing agent produced by a production method in accordance with an embodiment of the present invention are useful for an absorbent body for an absorbent article such as a disposable diaper, a sanitary napkin, and a blood absorbent for medical use. Further, the particulate water absorbing agent can also be variously used for a pet urine absorbent, a urine gelatinizer of a portable toilet, an agent for preserving freshness of vegetables, fruit, and the like, a drip absorbent for meat and fish, a refrigerant, a disposable body warmer, a battery gelatinizer, a water retention agent for plants, soil, and the like, a condensation preventing agent, a waterproofing agent, a packing agent, artificial snow, and the like.

REFERENCE SIGNS LIST

100 Measuring device
101 Cylindrical cell
102 Metal gauze
103 Particulate water absorbing agent
104 Piston
105 Weight
106 Metal vat
107 Glass filter
108 Filter paper
109 0.9% aqueous sodium chloride solution
200 Measuring device
201 Container
202 Glass tube
203 0.69% aqueous sodium chloride solution
204 Resin tube
205 Cock
250 Measuring device
251 Cylindrical cell
252 Metal gauze
254 Particulate water absorbing agent
255 Metal gauze
256 Piston
257 Hole
260 Lid
261 Weight
262 Metal vat
263 Glass filter
264 Synthesized urine
300 Rheometer
301 Dish (container section)
302 Swollen gel
303 Parallel plate (plate-shaped member)
304 Rotary shaft
400 Diffusion absorbency period measuring device
401 Acrylic resin tray
402 Double-side tape
403 Tissue
404 Absorbent body
405 Top sheet
406 Metal gauze
407 Inlet
408 Lid
409 Weight

The invention claimed is:

1. A particulate water absorbing agent having a polyacrylic acid (salt)-based water-absorbing resin as a main component, being surface-crosslinked and satisfying physical properties (1) to (3) below:
   (1) a proportion of particles with a particle diameter of not less than 150 μm and less than 850 μm is not less than 90% by weight;
   (2) an elastic modulus index (EMI) of particles with a particle diameter of not less than 500 μm and less than 600 μm is not less than 5500; and
   (3) a recovery rate defined as Rec.CRC/CRC is 1.05 to 1.20.

2. The particulate water absorbing agent according to claim 1, wherein said recovery rate in (3) above is 1.05 to 1.16.

3. The particulate water absorbing agent according to claim 1, wherein said elastic modulus index (EMI) in (2) above is 6000 to 9500.

4. The particulate water absorbing agent according to claim 1, wherein a fluid retention capacity under pressure (AAP) is not less than 20 g/g.

5. The particulate water absorbing agent according to claim 1, wherein a saline flow conductivity (SFC) is not less than $10 \times 10^{-7} \cdot cm^3 \cdot s \; g^{-1}$.

6. The particulate water absorbing agent according to claim 1, wherein a water absorption time according to a vortex method is not more than 42 seconds.

7. The particulate water absorbing agent according to claim 1, wherein a free swell rate (FSR) is not less than 0.28 g/(g·s).

8. The particulate water absorbing agent according claim 1, wherein said particulate water absorbing agent is surface-crosslinked by a covalent bonding surface-crosslinking agent.

9. The particulate water absorbing agent according to claim 1, wherein a proportion of particles with a particle diameter of less than 150 μm is not more than 5% by weight.

10. The particulate water absorbing agent according claim 1, further satisfying a physical property (4) below:
  (4) an elastic modulus index (EMI) of particles with a particle diameter of not less than 425 μm and less than 500 μm is not less than 4500.

11. The particulate water absorbing agent according to claim 10, further satisfying a physical property (5) below:
  (5) an elastic modulus index (EMI) of particles with a particle diameter of not less than 300 μm and less than 425 μm is not less than 3500.

12. The particulate water absorbing agent according to claim 1, having:
  (a) a proportion of particles with a particle diameter of not less than 150 μm and less than 300 μm being 5% by weight to 50% by weight;
  (b) a proportion of particles with a particle diameter of not less than 300 μm and less than 425 μm being 10% by weight to 60% by weight;
  (c) a proportion of particles with a particle diameter of not less than 425 μm and less than 500 μm being 5% by weight to 50% by weight;
  (d) a proportion of particles with a particle diameter of not less than 500 μm and less than 600 μm being 5% by weight to 50% by weight; and
  (e) a proportion of particles with a particle diameter of not less than 600 μm and less than 850 μm being 0.1% by weight to 50% by weight,
  wherein a sum of the proportions of the particles having the particle diameters each defined in (a) to (e) above is 90% by weight to 100% by weight.

13. The particulate water absorbing agent according to claim 1, wherein a weight average particle diameter (D50) is 300 μm to 500 μm and a logarithmic standard deviation ($\sigma\zeta$) is 0.25 to 0.45.

14. An absorbent body, comprising a particulate water absorbing agent according to claim 1.

15. An absorbent article, comprising a particulate water absorbing agent according to claim 1.

* * * * *